(12) United States Patent
Radesca et al.

(10) Patent No.: US 6,673,372 B1
(45) Date of Patent: Jan. 6, 2004

(54) CRYSTALLINE EFAVIRENZ

(75) Inventors: Lilian A. Radesca, Newark, DE (US); Michael B. Maurin, Wilmington, DE (US); Shelley R. Rabel, Landenberg, PA (US); James R. Moore, Newark, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 09/329,421

(22) Filed: Jun. 10, 1999

Related U.S. Application Data

(60) Provisional application No. 60/088,981, filed on Jun. 11, 1998.

(51) Int. Cl.$^7$ .............................. A61K 9/14; A61K 9/20
(52) U.S. Cl. ...................................... 424/489; 424/464
(58) Field of Search ................................ 424/464, 451, 424/455, 489

(56) References Cited

U.S. PATENT DOCUMENTS

| | | | |
|---|---|---|---|
| 5,519,021 A | * | 5/1996 | Young et al. ............ 514/230.5 |
| 5,965,729 A | | 10/1999 | Clarke et al. |
| 6,124,319 A | * | 9/2000 | MacCoss et al. ........... 514/318 |

FOREIGN PATENT DOCUMENTS

| | | |
|---|---|---|
| EP | 0582455 | 2/1994 |
| WO | 9520389 | 8/1995 |
| WO | 9637457 | 11/1996 |
| WO | 9804535 | 2/1998 |
| WO | 9814436 | 4/1998 |
| WO | WO 98/27073 | 6/1998 |
| WO | WO 98/45278 | 10/1998 |

OTHER PUBLICATIONS

PGPUB US 20020115664 A1, App. No. 10/000,537, filed Oct. 19, 2001.

* cited by examiner

Primary Examiner—James M. Spear
(74) Attorney, Agent, or Firm—Mary K. Van Atten

(57) ABSTRACT

The potent reverse transcriptase inhibitor Efavirenz is produced in crystalline form. Crystalline Efavirenz exists in several physical forms which are-designated Forms 1, 2, 3 and 4, and are characterized by x-ray powder diffraction and differential scanning calorimetry. Pharmaceutical compositions and methods are useful for the treatment of the human immunodeficiency virus (HIV).

45 Claims, 8 Drawing Sheets

CRYSTALLINE EFAVIRENZ

This application claims the benefit of U.S. Provisional Application No. 60/088,981, filed Jun. 11, 1998.

FIELD OF THE INVENTION

The potent reverse transcriptase inhibitor Efavirenz is produced in crystalline form. Crystalline Efavirenz exists in several physical forms which are designated Forms 1, 2, 3, 4, and 5 and are characterized by x-ray powder diffraction and differential scanning calorimetry. Pharmaceutical compositions and methods are useful for the treatment of the human immunodeficiency virus (HIV).

BACKGROUND OF THE INVENTION

Reverse transcription is a common feature of retrovirus replication. Viral replication requires a virally encoded reverse transcriptase to generate DNA copies of viral sequences by reverse transcription of the viral RNA genome. Reverse transcriptase, therefore, is a clinically relevant target for the chemotherapy of retroviral infections because the inhibition of virally encoded reverse transcriptase would interrupt viral replication.

Efavirenz is a compound which is effective in the treatment of the human immunodeficiency virus (HIV) which is the retrovirus that causes progressive destruction of the human immune system with the resultant onset of AIDS. Effective treatment through inhibition of HIV reverse transcriptase has been shown for both nucleoside based inhibitors, such as azidothymidine, and non-nucleoside based inhibitors. Benzoxazinones such as Efavirenz have been found to be useful non-nucleoside based inhibitors of HIV reverse transcriptase. Efavirenz is known by its chemical name, (S)-6-chloro-4-cyclopropylethynyl-4-trifluoromethyl-1,4-dihydro-2H-3,1-benzoxazin-2-one represented in formula (I):

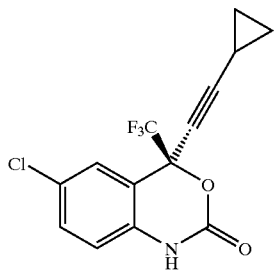

(I)

Efavirenz is not only a highly potent reverse transcriptase inhibitor, but is also efficacious against HIV reverse transcriptase resistance. Due to the importance of (S)-6-chloro-4-cyclopropylethynyl-4-trifluoromethyl-1,4-dihydro-2H-3,1-benzoxazin-2-one as a reverse transcriptase inhibitor, crystalline forms which exhibit chemical and physical advantages for manufacture, purification and formulation are necessary.

Treatment or prevention of the foregoing disorders is accomplished by administering a therapeutically effective amount of Efavirenz to a human or animal subject in need of such treatment or prevention. The treatment with Efavirenz may be accomplished by its use as a single compound, as a pharmaceutical composition ingredient, or in combination with other antivirals, immunomodulators, antibiotics and vaccines. The compound may be administered enterally or parenterally in solid or liquid dosage forms.

Efavirenz has not been known previously to exist in stable crystalline polymorphic forms. Accordingly, a need exists for stable crystalline forms of the drug and reliable and reproducible procedures for their manufacture.

SUMMARY OF THE INVENTION

In one aspect, the present invention is directed to crystalline Efavirenz. A related aspect resides in novel crystalline forms of Efavirenz, designated as Form 1, Form 2, Form 3, Form 4, and Form 5. These forms have been characterized and distinguished from one another by differential scanning calorimetry (DSC) and x-ray powder diffraction analysis.

Further aspects of the invention involve pharmaceutical compositions of crystalline Efavirenz and its five forms. The crystalline products of this invention may be formulated into conventional solid pharmaceutical dosage forms or used for the preparation of liquid dosage forms by combining a therapeutically effective amount of the crystalline drug with a pharmaceutically acceptable carrier. The crystalline products may be administered in pharmaceutical compositions which may combine other antivirals, immunomodulators, antibiotics or vaccines.

In another aspect, the present invention involves a method for inhibiting reverse transcriptase which comprises administering an amount of crystalline Efavirenz sufficient to result in reverse transcriptase being contacted with an effective inhibitory amount of the active drug substance.

In particular aspects, the invention involves methods for treating retroviral infections such as human immunodeficiency virus and disorders involving viral replication, which comprise administering a therapeutically effective amount of a pharmaceutical composition comprising the novel crystalline forms of Efavirenz of this invention.

It is another object of the present invention to provide a novel method for treating HIV infection which comprises administering to a host in need thereof a therapeutically effective combination of Form 1, 2, 3, 4, or 5 Efavirenz with and one or more compounds selected form the group consisting of HIV reverse transcriptase inhibitors and HIV protease inhibitors.

BRIEF DESCRIPTION OF THE DRAWINGS

The invention is illustrated by reference to the accompanying drawings described below.

DETAILED DESCRIPTION OF THE INVENTION

In a first embodiment, the present invention provides Form 1 of crystalline Efavirenz.

In a preferred embodiment, Form 1 crystalline Efavirenz is in substantially pure form.

In another preferred embodiment, the Form 1 crystalline Efavirenz is characterized by an x-ray powder diffraction pattern comprising four or more 2θ values selected from the group consisting of 6.0±0.2, 6.3±0.2, 10.3±0.2, 10.8±0.2, 14.1±0.2, 16.8±0.2, 20.0±0.2, 20.5±0.2, 21.1±0.2, and 24.8±0.2.

Figure 1:
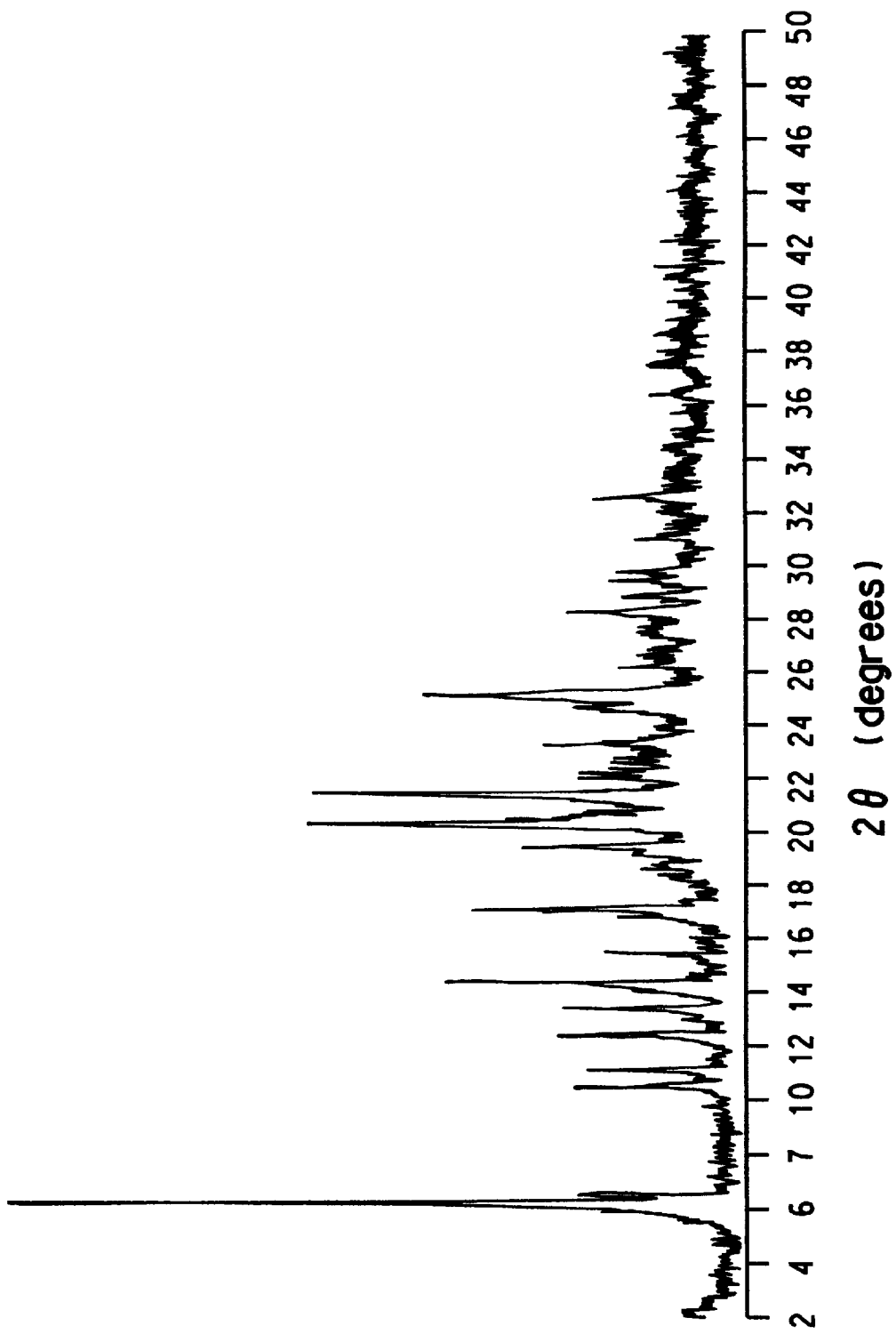
FIG. 1 shows a powder x-ray diffractogram of the Form 1 crystalline form of (S)-6-chloro-4-cyclopropylethynyl-4-trifluoromethyl-1,4-dihydro-2H-3,1-benzoxazin-2-one.

In another preferred embodiment, the Form 1 crystalline Efavirenz is characterized by an x-ray powder diffraction pattern substantially in accordance with that shown in FIG. 1.

In another preferred embodiment, the Form 1 crystalline Efavirenz is characterized by a differential scanning calorimetry thermogram having a peak at about 138° C. to about 140° C.

Figure 5:
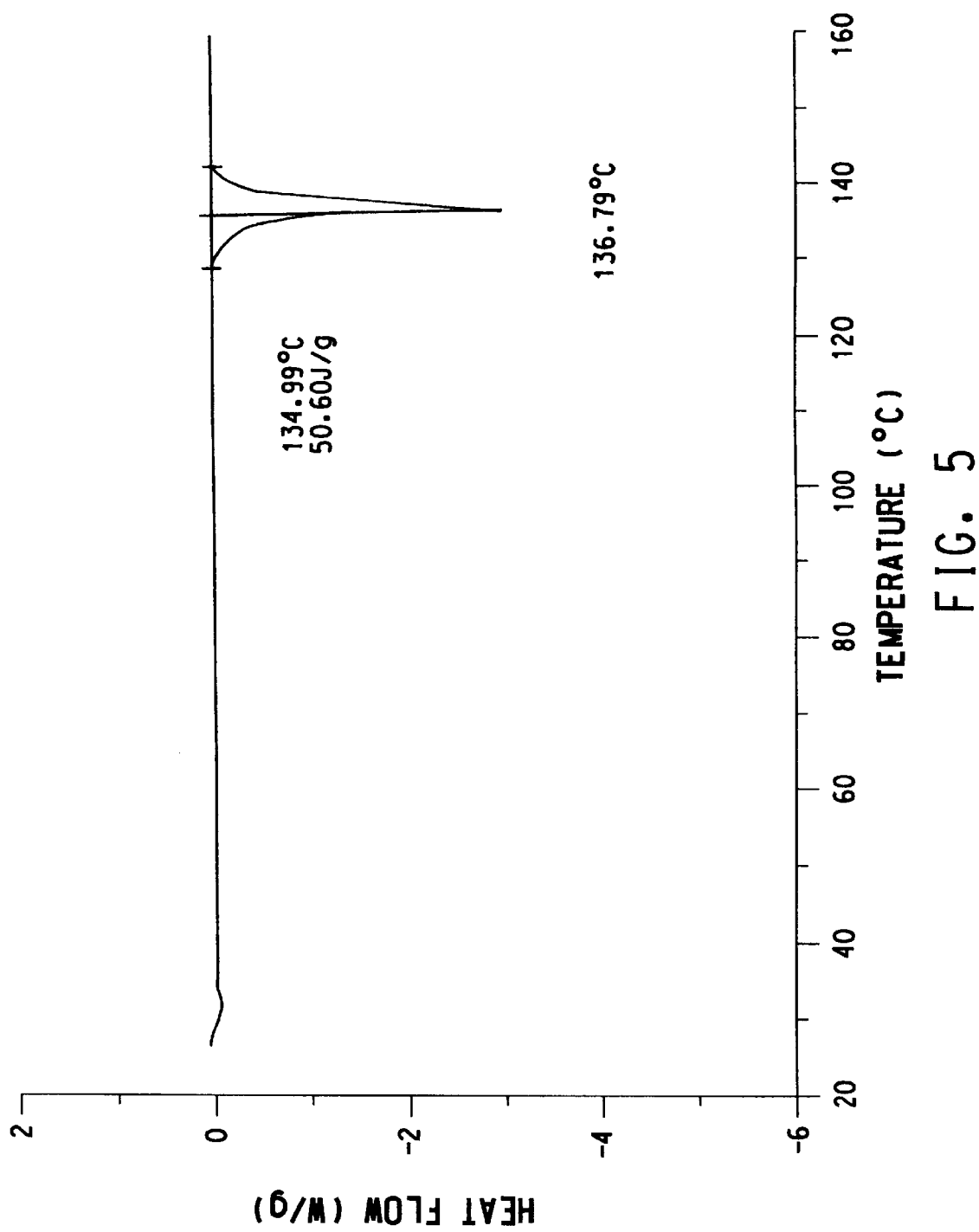
FIG. 5 shows a differential calorimetry thermogram of the Form 1 crystalline form of (S)-6-chloro-4-cyclopropylethynyl-4-trifluoromethyl-1,4-dihydro-2H-3,1-benzoxazin-2-one.

In another preferred embodiment, the Form 1 crystalline Efavirenz is characterized by a differential scanning calorimetry thermogram substantially in accordance with that shown in FIG. 5.

In a more preferred embodiment, the Form 1 crystalline Efavirenz is characterized by an x-ray powder diffraction pattern comprising four or more 2θ values selected from the group consisting of: 6.0±0.2, 6.3±0.2, 10.3±0.2, 10.8±0.2, 14.1±0.2, 16.8±0.2, 20.0±0.2, 20.5±0.2, 21.1±0.2, and 24.8±0.2, and further characterized by a differential scanning calorimetry thermogram having a peak at about 138° C. to about 140° C.

In another more preferred embodiment, the Form 1 crystalline Efavirenz is characterized by an x-ray powder diffraction pattern substantially in accordance with that shown in FIG. 1, and is further characterized by a differential scanning calorimetry thermogram having a peak at about 138° C. to about 140° C.

In a second embodiment, the present invention describes a pharmaceutical composition comprising a therapeutically effective amount of the Form 1 crystalline Efavirenz and a pharmaceutically acceptable carrier.

In a preferred embodiment, the pharmaceutical composition is contained in a capsule or compressed tablet dosage form, wherein the therapeutically effective amount is about 1 mg to about 1000 mg of Form 1 crystalline Efavirenz.

In a more preferred embodiment, the pharmaceutical composition is contained in a capsule or compressed tablet dosage form, wherein the therapeutically effective amount is about 50 mg to about 200 mg of Form 1 crystalline Efavirenz.

In another more preferred embodiment, the pharmaceutical composition contained in a capsule or compressed tablet contains greater than about 10% by weight of a disintegrant relative to the total dry weight of the dosage form.

In another preferred embodiment, the pharmaceutical composition is in liquid form.

In a more preferred embodiment, the liquid form comprises about 0.1 percent to about 15 percent by weight of Form 1 crystalline Efavirenz and a liquid vehicle comprising about 50 percent to about 99 percent by weight of polyolesters of medium chain fatty acids.

In an even more preferred embodiment, the composition is contained in a soft gelatin capsule, wherein the polyol esters of medium chain fatty acids consist essentially of $C_8$ to $C_{10}$ fatty acid triglycerides.

In another more preferred embodiment, the liquid form comprising about 0.1 percent to about 15 percent by weight of Form 1 crystalline Efavirenz and a liquid vehicle comprising about 50 percent to about 99 percent by weight of polyolesters of medium chain fatty acids contains a sweetening agent in a range of about 0.1 percent to about 50 percent by weight.

In another more preferred embodiment, the pharmaceutical composition which is in liquid form comprises about 0.1 percent to about 10 percent by weight of Form 1 crystalline Efavirenz and a liquid vehicle about 50 percent to about 99 percent by weight of vegetable oil.

In an even more preferred embodiment, the pharmaceutical composition is contained in a soft gelatin capsule, wherein the vegetable oil is soybean oil or peanut oil.

In another more preferred embodiment, the pharmaceutical composition which is in liquid form comprising about 0.1 percent to about 10 percent by weight of Form 1 crystalline Efavirenz and a liquid vehicle about 50 percent to about 99 percent by weight of vegetable oil, contains a sweetening agent in a range of about 1.0 percent to about 50 percent by weight.

In a third embodiment, a capsule or compressed tablet pharmaceutical dosage form comprises:
 (a) a therapeutically effective amount of Form 1 crystalline Efavirenz;
 (b) a surfactant;
 (c) a disintegrant;
 (d) a binder; and
 (e) a lubricant.

In a preferred embodiment, the therapeutically effective amount is about 50 mg to about 200 mg of Form 1 crystalline Efavirenz, the surfactant is sodium lauryl sulfate, the disintegrant is sodium starch glycolate, the binder is lactose and the lubricant is magnesium stearate.

In a fourth embodiment, the present invention describes a method for inhibiting viral replication by a virally encoded reverse transcriptase which comprises providing Form 1 crystalline Efavirenz, in an amount sufficient to result in the HIV reverse transcriptase being contacted with an effective inhibitory amount of the active drug substance.

In a preferred embodiment, the compound is provided to a human or animal subject to inhibit HIV reverse transcriptase in vivo.

In a fifth embodiment, the present invention describes a method for the treatment of human immunodeficiency virus infection which comprises administering to a host in need of such treatment a therapeutically effective amount of Form 1 crystalline Efavirenz.

In a preferred embodiment, the Form 1 crystalline Efavirenz is administered at a dosage from about 1 to about 1000 mg per dose.

In a more preferred embodiment, the Form 1 crystalline Efavirenz is administered at a dosage from about 50 mg to about 200 mg per dose.

In a sixth embodiment, Form 1 crystalline Efavirenz is prepared by recrystallization of Efavirenz from a hydrocarbon solvent.

In a seventh embodiment, Form 1 crystalline Efavirenz is prepared by the process comprising:
1) recrystallizing Efavirenz from a suitable solvent;
2) isolating the crystals; and
3) drying the crystals to an appropriate temperature to afford Form 1 crystalline Efavirenz in substantially pure form.

In a more preferred embodiment, the suitable solvent is heptane or a mixture of tetrahydrofuran and heptane, the crystals are isolated by filtration, the appropriate temperature is about 70° C. to about 95° C., and substantially pure is greater than 90 percent pure.

In an eighth embodiment, Form 1 crystalline Efavirenz is prepared by heating Form 2, Form 3, Form 4, or Form 5 Efavirenz or mixtures thereof.

In a ninth embodiment, Form 1 crystalline Efavirenz is prepared by stirring a slurry of Form 2 Efavirenz, Form 3 Efavirenz, or mixtures thereof in a hydrocarbon solvent.

In a tenth embodiment, the present invention describes Form 2 of crystalline Efavirenz.

In a preferred embodiment, Form 2 crystalline Efavirenz is in substantially pure form.

In another preferred embodiment, Form 2 crystalline Efavirenz is characterized by an x-ray powder diffraction pattern comprising four or more 2θ values selected from the group consisting of: 6.8±0.2, 9.2±0.2, 12.3±0.2, 16.2±0.2, 21.4±0.2, 22.7±0.2, 24.1±0.2, and 28.0±0.2.

Figure 2:
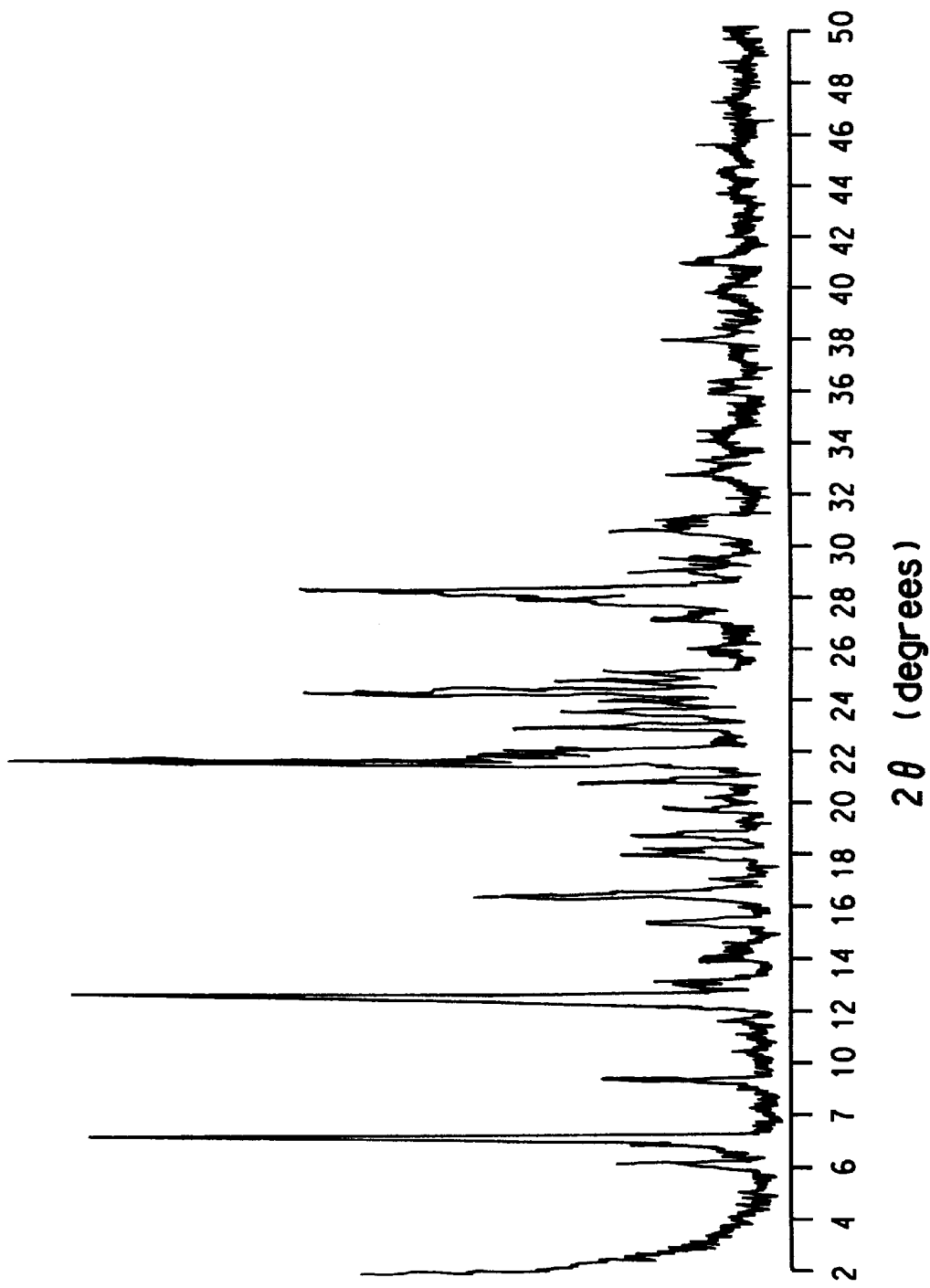
FIG. 2 shows a powder x-ray diffractogram of the Form 2 crystalline form of (S)-6-chloro-4-cyclopropylethynyl-4-trifluoromethyl-1,4-dihydro-2H-3,1-benzoxazin-2-one.

In another preferred embodiment, Form 2 crystalline Efavirenz is characterized by an x-ray powder diffraction pattern substantially in accordance with that shown in FIG. 2.

In another preferred embodiment, Form 2 crystalline Efavirenz is characterized by a differential scanning calorimetry thermogram having a peak at about 116° C. to about 119° C.

Figure 6:
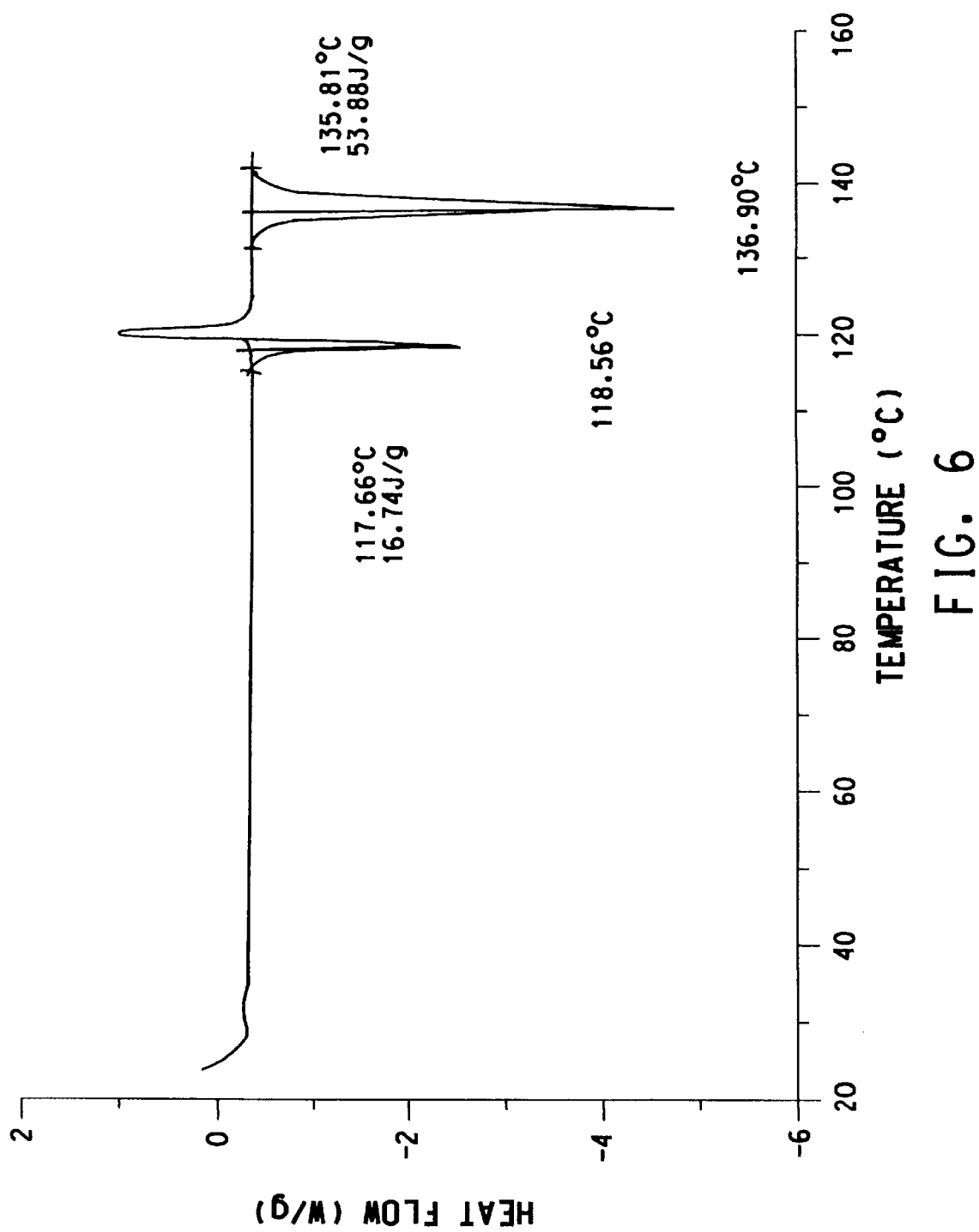
FIG. 6 shows a differential calorimetry thermogram of the Form 2 crystalline form of (S)-6-chloro-4-cyclopropylethynyl-4-trifluoromethyl-1,4-dihydro-2H-3,1-benzoxazin-2-one.

In another preferred embodiment, Form 2 crystalline Efavirenz is characterized by a differential scanning calorimetry thermogram substantially in accordance with that shown in FIG. 6.

In a more preferred embodiment, Form 2 crystalline Efavirenz is characterized by an x-ray powder diffraction pattern comprising four or more 2θ values selected from the group consisting of: 6.8±0.2, 9.2±0.2, 12.3±0.2, 16.2±0.2, 21.4±0.2, 22.7±0.2, 24.1±0.2, and 28.0±0.2, and further characterized by a differential scanning calorimetry thermogram having a peak at about 116° C. to about 119° C.

In another more preferred embodiment, Form 2 crystalline Efavirenz is characterized by an x-ray powder diffraction pattern substantially in accordance with that shown in FIG. 2, and further characterized by a differential scanning calorimetry thermogram having a peak at about 116° C. to about 119° C.

In an eleventh embodiment, the present invention describes a pharmaceutical composition comprising a therapeutically effective amount of Form 2 crystalline Efavirenz and a pharmaceutically acceptable carrier.

In a preferred embodiment, the pharmaceutical composition is contained in a capsule or compressed tablet dosage form, wherein the therapeutically effective amount is about 1 mg to about 1000 mg of Form 2 crystalline Efavirenz.

In another preferred embodiment, the pharmaceutical composition is in liquid form, wherein the therapeutically effective amount is about 0.1 percent to about 15 percent Form 2 crystalline Efavirenz.

In a twelfth embodiment, the present invention describes a method for inhibiting viral replication by a virally encoded reverse transcriptase which comprises providing Form 2 crystalline Efavirenz, in an amount sufficient to result in the HIV reverse transcriptase being contacted with an effective inhibitory amount of the active drug substance.

In a thirteenth embodiment, the present invention describes a method for the treatment of viral disorders, such as human immunodeficiency virus and other indications which comprises administering to a host in need of such treatment or prevention a therapeutically effective amount of Form 2 crystalline Efavirenz.

In a preferred embodiment, the Form 2 crystalline Efavirenz is administered at a dosage from about 1 to about 1000 mg per dose.

In a fourteenth embodiment, Form 2 crystalline Efavirenz is prepared by the process of rapid crystallization from a saturated alkane solution of Efavirenz.

In a preferred embodiment, rapid crystallization comprises:
1) dissolving Efavirenz in a suitable solvent at a suitable temperature to give a saturated solution;
2) filtering the saturated solution; and
3) cooling the saturated solution rapidly to produce Form 2 crystalline Efavirenz.

In a more preferred embodiment, the suitable solvent is heptane, the suitable temperature is about 70° C. to 80° C., and cooling the saturated solution rapidly comprises contacting the saturated solution with a cold surface.

In a fifteenth embodiment, the present invention describes Form 3 of crystalline Efavirenz in substantially pure form.

In another preferred embodiment, Form 3 crystalline Efavirenz is characterized by an x-ray powder diffraction pattern comprising four or more 2θ values selected from the group consisting of: 7.1±0.2, 7.3±0.2, 11.0±0.2, 13.8±0.2, 20.9±0.2, 23.3±0.2, 27.9±0.2, and 33.5±0.2.

Figure 3:
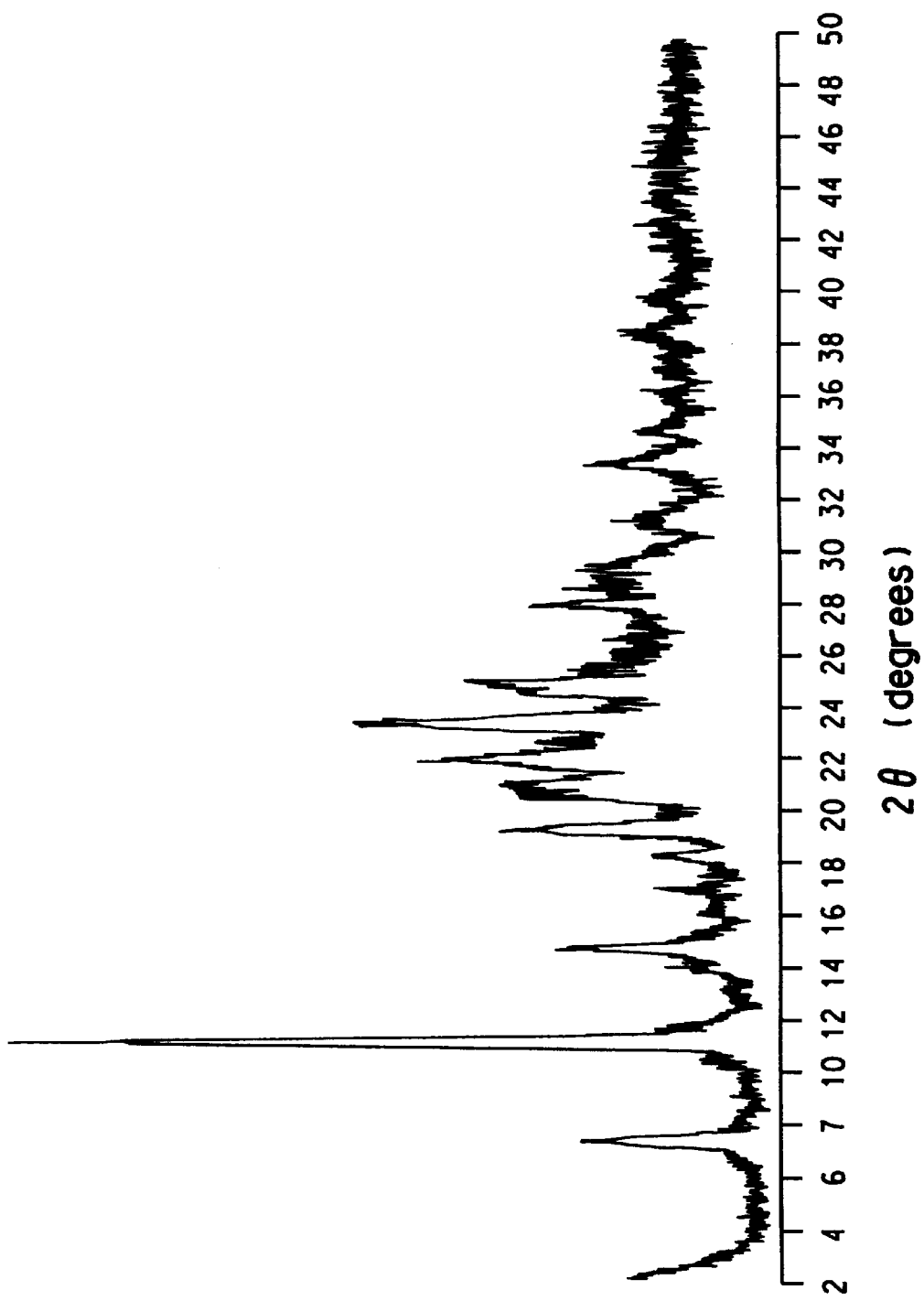
FIG. 3 shows a powder x-ray diffractogram of the Form 3 crystalline form of (S)-6-chloro-4-cyclopropylethynyl-4-trifluoromethyl-1,4-dihydro-2H-3,1-benzoxazin-2-one.

In another preferred embodiment, Form 3 crystalline Efavirenz is characterized by an x-ray powder diffraction pattern substantially in accordance with that shown in FIG. 3.

In another preferred embodiment, Form 3 crystalline Efavirenz is characterized by a differential scanning calorimetry thermogram having a peak at about 108° C. to about 110° C.

Figure 7:
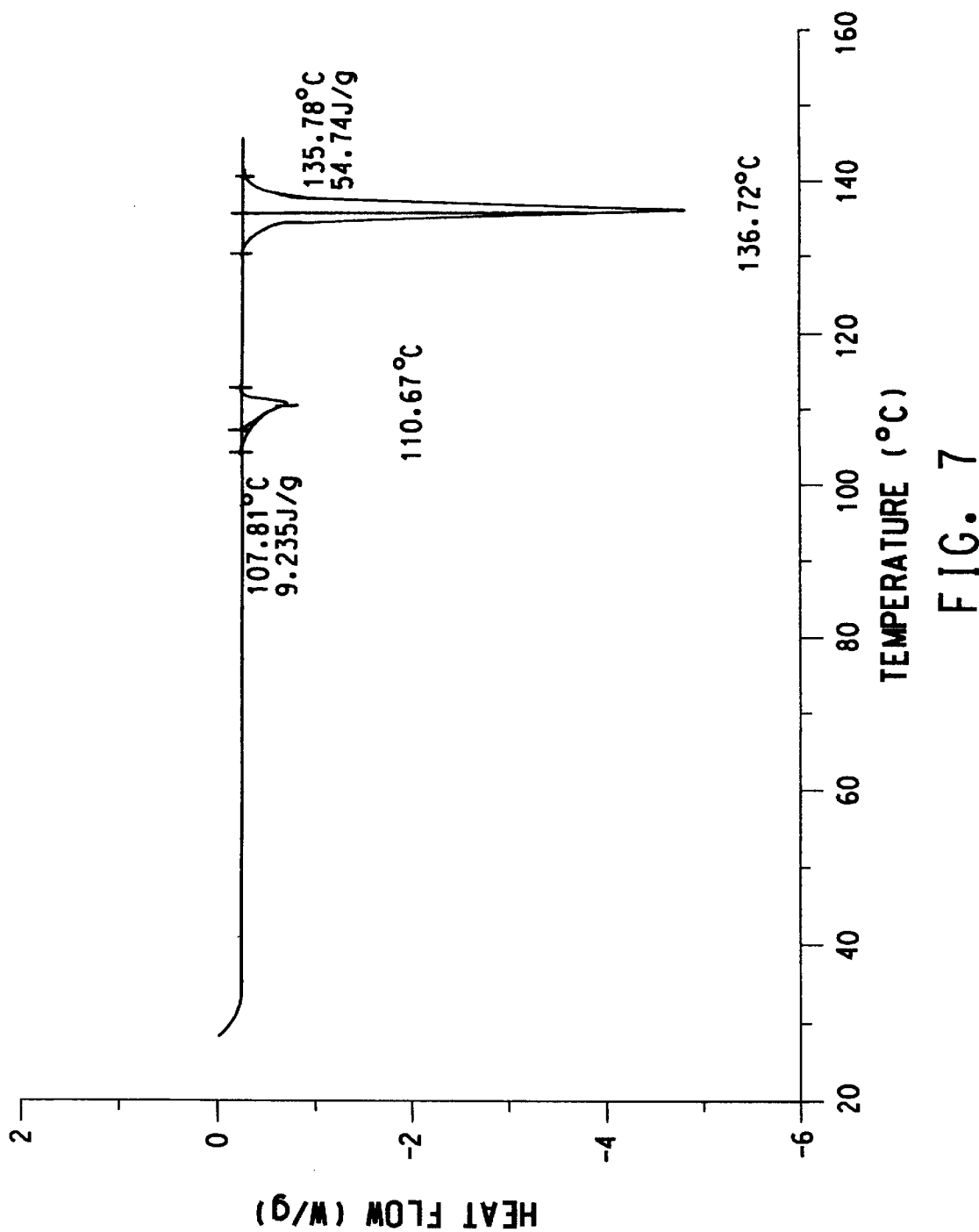
FIG. 7 shows a differential calorimetry thermogram of the Form 3 crystalline form of (S)-6-chloro-4-cyclopropylethynyl-4-trifluoromethyl-1,4-dihydro-2H-3,1-benzoxazin-2-one.

In another preferred embodiment, Form 3 crystalline Efavirenz is characterized by a differential scanning calorimetry thermogram substantially in accordance with that shown in FIG. 7.

In a more preferred embodiment, Form 3 crystalline Efavirenz is characterized by an x-ray powder diffraction pattern comprising four or more 2θ values selected from the group consisting of: 7.1±0.2, 7.3±0.2, 11.0±0.2, 13.8±0.2, 20.9±0.2, 23.3±0.2, 27.9±0.2, and 33.5±0.2, and further characterized by a differential scanning calorimetry thermogram having a peak at about 108° C. to about 110° C.

In another more preferred embodiment, Form 3 crystalline Efavirenz is characterized by an x-ray powder diffraction pattern substantially in accordance with that shown in FIG. 3, and further characterized by a differential scanning calorimetry thermogram having a peak at about 108° C. to about 110° C.

In a sixteenth embodiment, the present invention describes a pharmaceutical composition comprising a therapeutically effective amount of Form 3 crystalline Efavirenz and a pharmaceutically acceptable carrier.

In a preferred embodiment, the pharmaceutical composition is contained in a capsule or compressed tablet dosage form, wherein the therapeutically effective amount is about 1 mg to about 1000 mg of Form 3 crystalline Efavirenz.

In another preferred embodiment, the pharmaceutical composition is in liquid form, wherein the therapeutically effective amount is about 0.1 percent to about 15 percent Form 3 crystalline Efavirenz.

In a seventeenth embodiment, the present invention describes a method for inhibiting viral replication by a virally encoded reverse transcriptase which comprises providing Form 3 crystalline Efavirenz, in an amount sufficient to result in the HIV reverse transcriptase being contacted with an effective inhibitory amount of the active drug substance.

In an eighteenth embodiment, the present invention describes a method for the treatment of human immunodeficiency virus infection comprises administering to a host in need of such treatment or prevention a therapeutically effective amount of Form 3 crystalline Efavirenz.

In a preferred embodiment, the Form 3 crystalline Efavirenz is administered at a dosage from about 1 to about 1000 mg per dose.

In a nineteenth embodiment, Form 3 crystalline Efavirenz is prepared by the process of stirring a slurry of Form 1 Efavirenz, Form 2 Efavirenz or a mixture thereof, in a hydrocarbon solvent and isolating the crystals.

In a preferred embodiment, the hydrocarbon is heptane and the crystals are isolated by filtration.

In a twentieth embodiment, the present invention describes Form 4 of crystalline Efavirenz.

In a preferred embodiment, Form 4 of crystalline Efavirenz is in substantially pure form.

In another preferred embodiment, Form 4 crystalline Efavirenz is characterized by an x-ray powder diffraction pattern comprising four or more 2θ values selected from the group consisting of: 3.6±0.2, 6.3±0.2, 9.7±0.2, 11.0±0.2, 12.7±0.2, 13.2±0.2, 16.1±0.2, 19.2±0.2, 19.5±0.2, 20.6±0.2, and 24.3±0.2.

Figure 4:
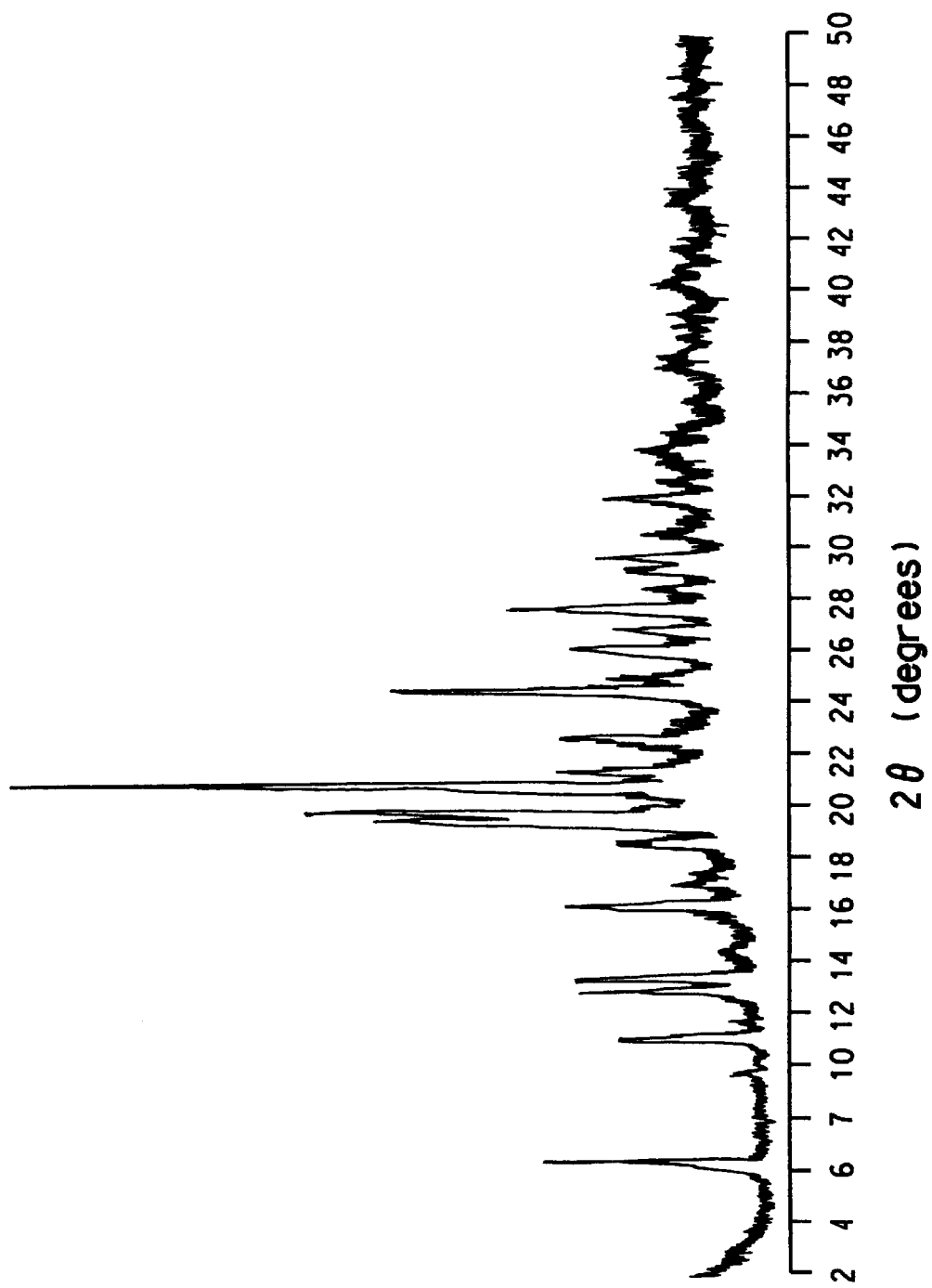
FIG. 4 shows a powder x-ray diffractogram of the Form 4 crystalline form of (S)-6-chloro-4-cyclopropylethynyl-4-trifluoromethyl-1,4-dihydro-2H-3,1-benzoxazin-2-one.

In another preferred embodiment, Form 4 crystalline Efavirenz is characterized by an x-ray powder diffraction pattern substantially in accordance with that shown in FIG. 4.

In another preferred embodiment, Form 4 crystalline Efavirenz is characterized by a differential scanning calorimetry thermogram having a peak at about 95° C. to about 100° C.

Figure 8:
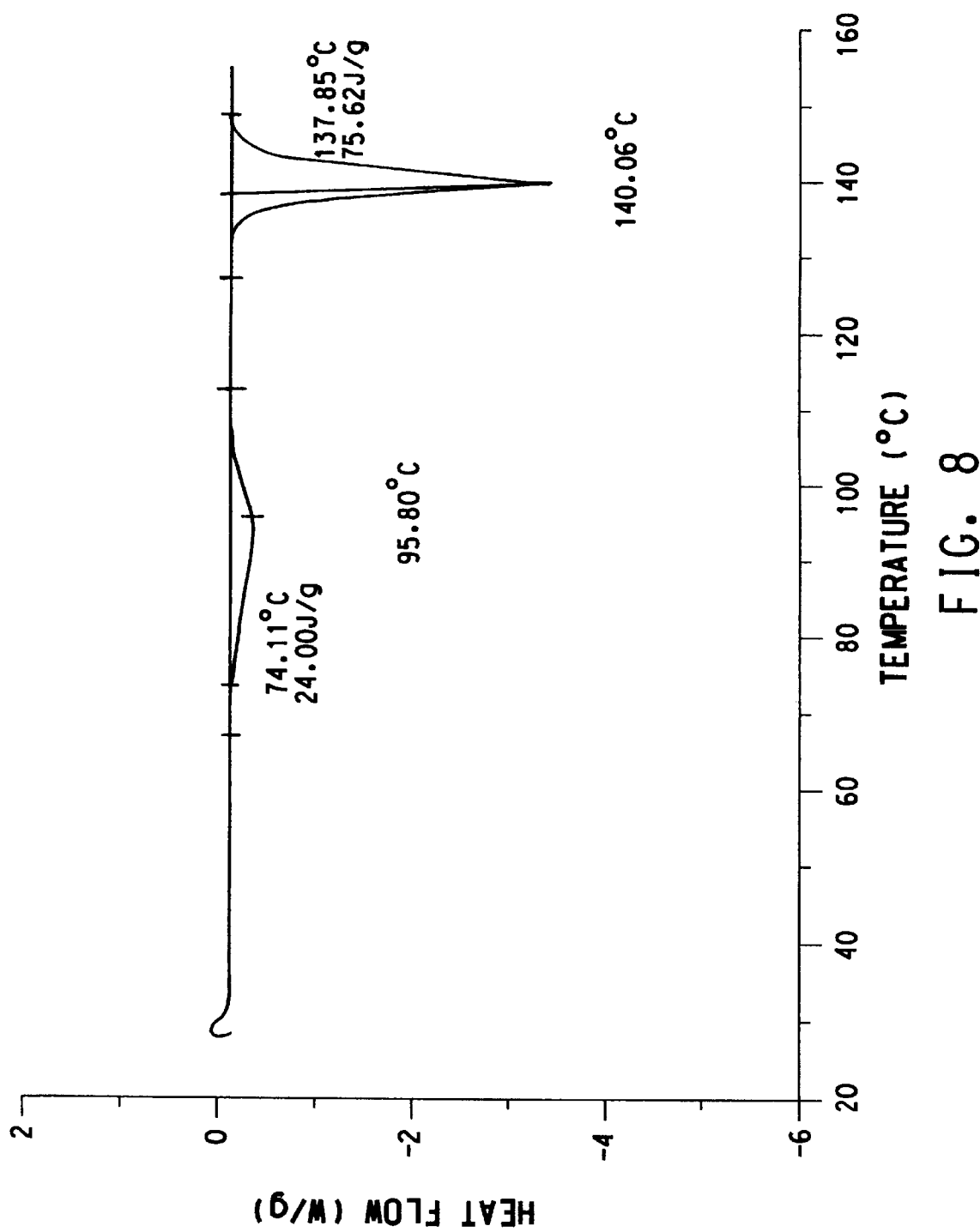
FIG. 8 shows a differential calorimetry thermogram of the Form 4 crystalline form of (S)-6-chloro-4-cyclopropylethynyl-4-trifluoromethyl-1,4-dihydro-2H-3,1-benzoxazin-2-one.

In another preferred embodiment, Form 4 crystalline Efavirenz is characterized by a differential scanning calorimetry thermogram substantially in accordance with that shown in FIG. 8.

In a more preferred embodiment, Form 4 crystalline Efavirenz is characterized by an x-ray powder diffraction pattern comprising four or more 2θ values selected from the group consisting of: 3.6±0.2, 6.3±0.2, 9.7±0.2, 11.0±0.2, 12.7±0.2, 13.2±0.2, 16.1±0.2, 19.2±0.2, 19.5±0.2, 20.6±0.2, and 24.3±0.2, and further characterized by a differential scanning calorimetry thermogram having a peak at about 95° C. to about 100° C.

In another more preferred embodiment, Form 4 crystalline Efavirenz is characterized by an x-ray powder diffraction pattern substantially in accordance with that shown in FIG. 4, and is further characterized by a differential scanning calorimetry thermogram having a peak at about 95° C. to about 100° C.

In a twenty-first embodiment, the present invention describes a pharmaceutical composition comprising a therapeutically effective amount of Form 4 crystalline Efavirenz and a pharmaceutically acceptable carrier.

In a preferred embodiment, the pharmaceutical composition is contained in a capsule or compressed tablet dosage form, wherein the therapeutically effective amount is about 1 mg to about 1000 mg of Form 4 crystalline Efavirenz.

In another preferred embodiment, the pharmaceutical composition is in liquid form, wherein the therapeutically effective amount is about 0.1 percent to about 15 percent Form 4 crystalline Efavirenz.

In a twenty-second embodiment, the present invention describes a method for inhibiting viral replication by a virally encoded reverse transcriptase which comprises providing Form 4 crystalline Efavirenz, in an amount sufficient to result in the HIV reverse transcriptase being contacted with an effective inhibitory amount of the active drug substance.

In a twenty-third embodiment, the present invention describes a method for the treatment of human immunodeficiency virus infection which comprises administering to a host in need of such treatment or prevention a therapeutically effective amount of Form 4 crystalline Efavirenz.

In a preferred embodiment, the Form 4 crystalline Efavirenz is administered at a dosage from about 1 to about 1000 mg per dose.

In a twenty-fourth embodiment, Form 4 crystalline Efavirenz is prepared by recrystallization from a mixed solvent system.

In a twentyfifth embodiment, Form 4 crystalline Efavirenz is prepared by the process comprising:
1) adding a suitable solvent to a solution of Efavirenz to produce a final solution;
2) distilling the final solution to a solvent composition from which Efavirenz crystallizes as Form 4 crystals; and
3) isolating the crystals.

In a preferred embodiment, the suitable solvent is heptane, the solution comprises of tetrahydrofuran and Efavirenz, the solvent composition is about 1 to about 10 percent tetrahydrofuran in heptane, and isolating comprises of filtering.

In a twentysixth embodiment, the present invention describes Form 5 of crystalline Efavirenz.

In a preferred embodiment, Form 5 of crystalline Efavirenz is in substantially pure form.

In another preferred embodiment, Form 5 crystalline Efavirenz is characterized by an x-ray powder diffraction pattern comprising four or more 2θ values selected from the group consisting of: 10.2±0.2, 11.4±0.2, 11.6±0.2, 12.6±0.2, 19.1±0.2, 20.6±0.2, 21.3±0.2, 22.8±0.2, 24.8±0.2, 27.4±0.2, 28.2±0.2, and 31.6±0.2.

In another preferred embodiment, Form 5 crystalline Efavirenz is characterized by a differential scanning calorimetry thermogram having a peak at about 108° C. to about 110° C.

In a more preferred embodiment, Form 5 crystalline 10 Efavirenz is characterized by an x-ray powder diffraction pattern comprising four or more 2θ values selected from the group consisting of: 10.2±0.2, 11.4±0.2, 11.6±0.2, 12.6±0.2, 19.1±0.2, 20.6±0.2, 21.3±0.2, 22.8±0.2, 24.8±0.2, 27.4±0.2, 28.2±0.2, and 31.6±0.2, and further characterized by a differential scanning calorimetry thermogram having a peak at about 108° C. to about 110° C.

In another more preferred embodiment, Form 5 crystalline Efavirenz is characterized by an x-ray powder diffraction pattern substantially in accordance with that shown in FIG. 9, and is further characterized by a differential scanning calorimetry thermogram having a peak at about 108° C. to about 110° C.

In a twenty-seventh embodiment, the present invention describes a pharmaceutical composition comprising a therapeutically effective amount of Form 5 crystalline Efavirenz and a pharmaceutically acceptable carrier.

In a preferred embodiment, the pharmaceutical composition is contained in a capsule or compressed tablet dosage form, wherein the therapeutically effective amount is about 1 mg to about 1000 mg of Form 5 crystalline Efavirenz.

In another preferred embodiment, the pharmaceutical composition is in liquid form, wherein the therapeutically effective amount is about 0.1 percent to about 15 percent Form 5 crystalline Efavirenz.

In a twenty-eighth embodiment, the present invention describes a method for inhibiting viral replication by a virally encoded reverse transcriptase which comprises providing Form 5 crystalline Efavirenz, in an amount sufficient to result in the HIV reverse transcriptase being contacted with an effective inhibitory amount of the active drug substance.

In a twenty-ninth embodiment, the present invention describes a method for the treatment of human immunodeficiency virus infection which comprises administering to a host in need of such treatment or prevention a therapeutically effective amount of Form 5 crystalline Efavirenz.

In a preferred embodiment, the Form 5 crystalline Efavirenz is administered at a dosage from about 1 to about 1000 mg per dose.

In a thirtieth embodiment, Form 5 crystalline Efavirenz is prepared by recrystallization from a mixed solvent system.

In a thirty-first embodiment, the present invention describes a method of treating HIV infection which comprises administering, in combination, to a host in need thereof a therapeutically effective amount of:
 (a) Form 1, 2, 3, 4 or 5 of crystalline Efavirenz; and
 (b) at least one compound selected from the group consisting of HIV reverse transcriptase inhibitors and HIV protease inhibitors.

In a thirty-second embodiment, the present invention describes a pharmaceutical composition comprising a therapeutically effective amount of Form 1, Form 2, Form 3, Form 4, Form 5 or mixtures thereof and a pharmaceutically acceptable carrier.

Efavirenz is known by its chemical name, (S)-6-chloro-4-cyclopropylethynyl-4-trifluoromethyl-1,4-dihydro-2H-3,1-benzoxazin-2-one represented by formula (I):

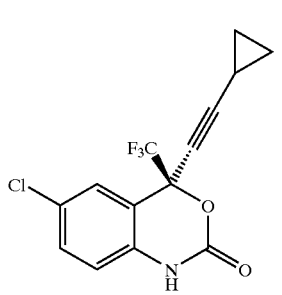

(I)

Synthesis of (S)-6-chloro-4-cyclopropylethynyl-4-trifluoromethyl-1,4-dihydro-2H-3,1-benzoxazin-2-one can be accomplished through the use of commercially available 4-chloroaniline. After reaction with pivaloyl chloride in the presence of hydroxide to afford the corresponding amide, treatment with an alkyl lithium and ethyl triflouroacetate is followed by acidification with a mineral acid to provide the salt of the triflouroketone (Scheme 1).

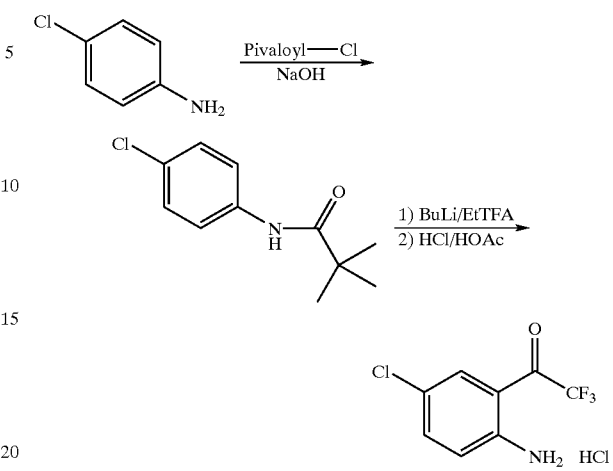

Scheme 1

The free base is subsequently reacted with a benzylic alcohol in the presence of acid to afford the benzylamine, which is alkylated in the presence of a chiral inducing agent with cyclopropylethynyl lithium to give the chiral alcohol (Scheme 2).

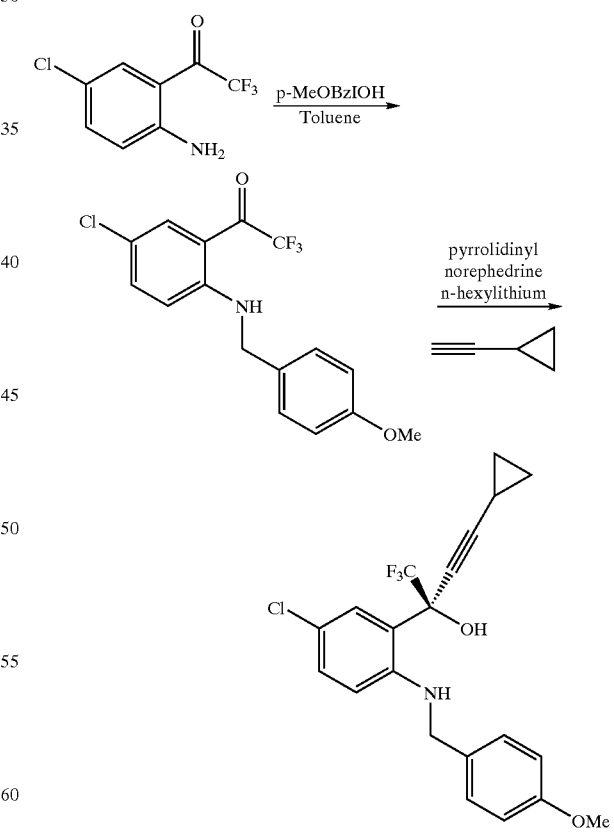

Scheme 2

The carbinol is oxidized to the benzylic imine, which undergoes an intramolecular cyclization. The benzyl group is removed, and the free amine cyclized to give the active drug substance represented by formula (I) (Scheme 3).

Scheme 3

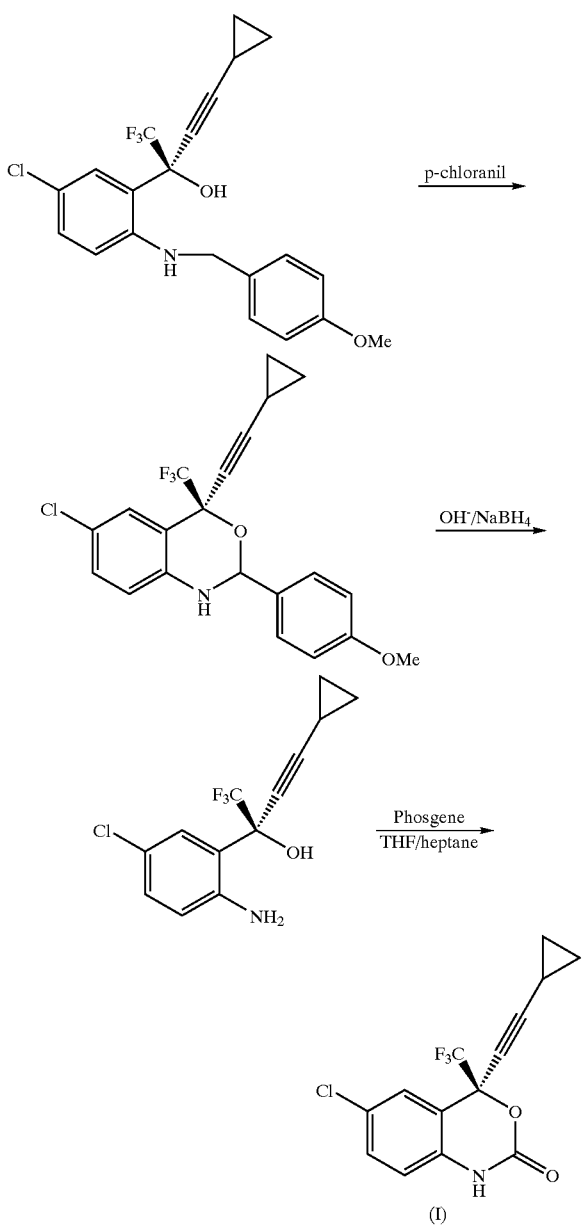

Methods for the synthetic preparation of Efavirenz are further disclosed in commonly assigned U.S. patent application Ser. No. 60/032,980, now U.S. Pat. No. 5,932,726, which is hereby incorporated by reference.

Five Forms designated as Form 1, Form 2, Form 3, form 4, Form 5 have been identified. Each Form is distinguishable from the other forms by x-ray powder diffraction (XRD) and differential scanning calorimetry (DSC). Each form can be isolated in substantially pure form under the conditions described. Further, the forms may be interconverted by procedures taught herein.

Form 1 is the most thermodynamically stable form. It has a melting point of about 138° C. to about 140° C., which is the highest of the four forms. Due to its increased stability, it is commonly used for drug formulation. All other forms may be converted into Form 1 during drying at about 60° C. to about 110° C. Conversion and drying is preferably done in a dryer oven at about 70° C. to about 110° C. under reduced pressure. More preferred is about 75° C. to about 85° C. Form 5 is converted to Form 1 by heating to 95° C under reduced pressure. Forms 2 and 3 may also be converted into Form 1 using a hydrocarbon slurry at about 65° C. to about 75° C. Heptane is the most preferred hydrocarbon for this conversion. Form 4, however, may not convert to Form 1 under these conditions because it is soluble at about 70° C. Form 1 may be directly crystallized from heptane when the saturated solution is seeded at about 60° C. to about 75° C. and held at about this temperature until Form 1 starts crystallizing.

Form 2 may be obtained by rapid crystallization. Rapid crystallization may be accomplished by the filtration of a saturated heptane solution of Efavirenz at about 70° C. to about 80° C., and crystallization preferably occurs when the solution is contacted with a cooler surface. Form 2 has a melting point of about 116° C. to about 119° C., observed by differential scanning calorimetry, and as such has exceptional stability. The needles are generally larger than the other forms. Form 2 rejects a variety of impurities common to the process which produces Efavirenz. Form 2 is therefore an important tool for commercial manufacture of Efavirenz concerning purification of second crops, and the recovery of batches which fail drug specifications. Further, the larger crystal size imparts numerous process advantages such as shortening filtration and drying time, and improving the flowability of slurry solutions. Form 2 may be converted into Form 1 by heating in a drier to about 95° C. to 100° C. for about 15 hours. Alternatively, Form 1 may be prepared from Form 2 by slurrying Form 2 in heptane heated to about 70° C. and holding for about 2 hours. The preferred concentration of this slurry is about 12 mL of solvent per gram of Form 2 Efavirenz.

Form 2 may also be converted into Form 3 by slurrying in heptane at room temperature for about 8 to about 24 hours. Form 2 may be converted into Form 4 by slurrying Form 2 into heptane to achieve a concentration of about 10 mL solvent per gram of Efavirenz and adding THF to reach a concentration of about 4 to about 6 mL THF in about 100 mL of heptane/THF solution.

Form 3 may be obtained by stirring a hydrocarbon slurry of Form 1 or Form 2 at about 25° C. Heptane is the most preferred hydrocarbon. In general, Form 2 converts faster to Form 3 than Form 1. This conversion takes about 8 hours to about to 24 hours. The conversion of Form 1 to Form 3 takes about a minimum of about 48 hours. Form 3 has a melting point of about 108° C. to about 110° C., observed by differential scanning calorimetry, and is the most stable form in solution slurries of Efavirenz at room temperature. Form 3 may be converted into Form 1 by drying at about 85° C. to about 90° C. for about 12 to about 24 hours. The conversion of Form 3 to Form 1 may also be accomplished by heating a heptane slurry having a concentration of about 10 mL to 14 mL of solvent per gram of Form 3 Efavirenz to about 65° C. to about 75° C., and holding the slurry at this temperature for about 2 hours.

Form 4 has a melting point of about 95° C. to about 100° C., observed by differential scanning calorimetry. Form 4 has the most suitable morphology following drying which leads to process advantages related to the handling of the crystalline material. Further, Form 4 possesses a preferred crystal shape, and may therefore be particularly well suited for formulation. The crystals may be obtained from a hydrocarbon slurry of Form 1 or Form 2 when a cyclic ether such as tetrahydrofuran (THF) is added to result in about a 4 to about 6 percent THF to hydrocarbon (v/v) solvent composition. Heptane is the most preferred hydrocarbon. It can be directly crystallized from about a 5% THF in heptane solution. The solubility of Efavirenz in THF/heptane mixtures is generally high, so in order to maximize yield, certain process protocol is preferably followed. Once Form 4 has crystallized, the THF concentration is preferably reduced to about less than 1%, which is accomplished by solvent exchange with heptane. Form 4 has also been obtained by crystallization from a saturated solution in methylcyclohexane. Recrystallization from straight heptane generally results in the formation of Forms 4, 1, 2 or mixtures thereof. Because Form 4 is the form which most commonly results when Efavirenz is crystallized from hydrocarbon/THF mixtures, it is the form which is isolated as a wet cake in the commercial drug manufacture. Form 4 may be converted to Form 1 by drying the crystals at about 80° C. to about 100° C. for about 12 to about 24 hours, preferably in a vacuum dryer.

For large scale preparations of Form 1 from Form 4, it is preferable for processing concerns to heat the wet cake of Form 4 to about 30 to about 50 to expel the majority of the solvent, after which the temperature may be elevated to about 80° C. to about 100° C. to complete the conversion.

Form 5 has a melting point of about 108° C. to about 110° C., observed by differential scanning calorimetry. Form 5 has been determined to be the most thermodynamically stable crystalline form below 40° C. Form 5 is highly crystalline and had the additional property of preferentially excluding impurities which leads to process advantages. The crystals may be obtained by recrystallization from a dilute solution of THF/heptane. The crystals may be obtained from solutions in which either Form 1 or Form 4 have already been isolated.

The possible interconversions of the forms of the present invention may be further understood by reference to Scheme 4.

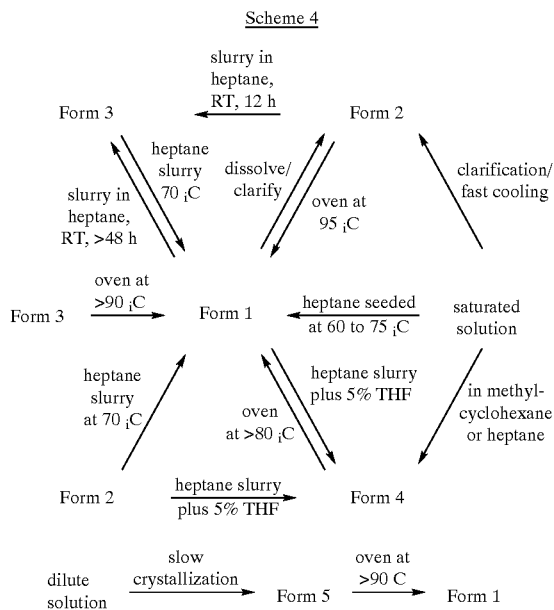

Scheme 4

Definitions

The following abbreviations are used herein: "THF" is intended to mean tetrahydrofuran, "GC" as used herein is intended to mean gas chromatography, "DMSO" is intended to mean dimethylsulfoxide, "TMEDA" is intended to mean N,N,N'N'-tetramethylethylenediamine.

The term "hydrocarbon" as used herein, refers to alkane solvents. Examples include but are not limited to solvents such as pentane, hexane, heptane, octane, nonane, decane and the like. Preferred mixed solvent systems in the present invention are mixed solvent systems comprising of tetrahydrofuran and hydrocarbons.

The term "slurry" as used herein is intended to mean a saturated solution of Efavirenz and an additional amount of Efavirenz to give a heterogeneous solution of Efavirenz and a solvent.

The present invention describes Form 1 Efavirenz, Form 2 Efavirenz, Form 3 Efavirenz, Form 4 Efavirenz, and Form 5 Efavirenz in substantially pure form. As used herein, "substantially pure" means a compound having a purity greater than 90 percent, including 90, 91, 92, 93, 94, 95, 96, 97, 98, 99, and 100 percent.

When dissolved, Efavirenz loses its crystalline structure, and is therefore referred to as a solution of Efavirenz. All forms of the present invention, however, may be used for the preparation of liquid formulations in which the drug is dissolved or suspended. In addition, the crystalline Efavirenz may be incorporated into solid formulations.

A therapeutically effective amount of the crystalline Efavirenz is combined with a pharmaceutically acceptable carrier to produce the pharmaceutical compositions of this invention. By "therapeutically effective amount" it is meant an amount that, when administered alone or with an additional therapeutic agent, is effective to prevent, suppress or ameliorate the disease or condition or the progression of the disease or condition. The combination of compounds described herein is preferably a synergistic combination. Synergy, as described for example by Chou and Talalay, Adv. Enzyme Regul. 22:27–55 (1984), occurs when the effect (in this case, inhibition of HIV replication) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

The compounds of the present invention are useful in the inhibition of HIV reverse transcriptase, treatment of infection by human immunodeficiency virus (HIV) and the treatment of consequent pathological conditions such as acquired immunodeficiency syndrome (AIDS). Treating AIDS, or treating infection by HIV is defined as including, but not limited to, treatment and prevention of a wide range of states of HIV infection: AIDS, ARC (AIDS related complex), both symptomatic and a symptomatic, and actual or potential exposure to HIV by blood transfusion, exchange of bodily fluids, bites, accidental needle stick, or exposure to blood during surgery.

For these purposes, the compounds of the present invention may be administered orally, parenterally (including subcutaneous injections, intraveneous, intramuscular, intrasternal injection or infusion techniques), by inhalation spray, rectally, in dosage unit formulations containing conventional non-toxic pharmaceutically acceptable adjuvants and vehicles, all using dosage forms well known to those of ordinary skill in the pharmaceutical arts.

The crystalline forms of Efavirenz described herein may be formulated into pharmaceutical compositions and employed in therapeutic and prophylactic methods as described in U.S. Pat. No. 5,519,021, which is hereby incorporated by reference. These methods include the direction of the forms of the present invention to combinations with one or more agents useful in the treatment of AIDS such as other HIV reverse transcriptase inhibitors, HIV protease inhibitors, antivirals, immunomodulators, antibiotics antiinfectives, or vaccines.

As used herein, "HIV reverse transcriptase inhibitor" is intended to refer to both nucleoside and non-nucleoside inhibitors of HIV reverse transcriptase (RT). Examples of nucleoside RT inhibitors include, but are not limited to, AZT, ddC, ddI, d4T, and 3TC. Examples of non-nucleoside RT inhibitors include, but are no limited to, delavirdine (Pharmacia and Upjohn U90152S), nevirapine (Boehringer Ingelheim), Ro 18,893 (Roche), trovirdine (Lilly), MKC-442 (Triangle), HBY 097 (Hoechst), ACT (Korean Research Institute), UC-781 (Rega Institute), UC-782 (Rega Institute), RD4-2025 (Tosoh Co. Ltd.), and MEN 10979 (Menarini Farmaceutici).

As used herein, "HIV protease inhibitor" is intended to refer to compounds which inhibit HIV protease. Examples include, but are not limited, saquinavir (Roche, Ro3-8959), ritonavir (Abbott, ABT-538), indinavir (Merck, MK-639), amprenavir (Vertex/Glaxo Wellcome), nelfinavir (Agouron, AG-1343), palinavir (Boehringer Ingelheim), BMS-232623 (Bristol-Myers Squibb), GS3333 (Gilead Sciences), KNI-413 (Japan Energy), KNI-272 (Japan Energy), LG-71350 (LG Chemical), CGP-61755 (Ciba-Geigy), PD 173606 (Parke Davis), PD 177298 (Parke Davis), PD 178390 (Parke Davis), PD 178392 (Parke Davis), U-140690 (Pharmacia and Upjohn), and ABT-378. Additional examples include the cyclic protease inhibitors disclosed in WO 93/07128, WO 94/19329, WO 94/22840, and PCT Application Number US 96/03426.

The crystalline forms of Efavirenz of this invention may be administered in oral dosage forms such as tablets, capsules (each of which includes sustained release or timed release formulations), pills, powders, granules, elixirs, tinctures, suspensions, syrups, and emulsions.

Solid dosage forms (pharmaceutical compositions) suitable for administration may generally contain from about 1 mg to about 1000 mg of crystalline Efavirenz per dosage unit.

For oral administration in solid form such as a tablet or capsule, the crystalline Efavirenz can be combined with a non-toxic, pharmaceutically acceptable inert carrier, such as lactose, starch, sucrose, glucose, methylcellulose, magnesium stearate, dicalcium phosphate, calcium sulfate, mannitol, sorbitol and the like.

Preferably, in addition to the active ingredient, solid dosage forms contain a number of additional ingredients referred to herein as "excipients". These excipients include among others diluents, binders, lubricants, glidants and disintegrants. Coloring agents may also be incorporated. "Diluents" as used herein, are agents which impart bulk to the formulation to make a tablet a practical size for compression. Examples of diluents are lactose and cellulose. "Binders" as used herein, are agents used to impart cohesive qualities to the powered material ensuring the tablet will remain intact after compression, as well as improving the free-flowing qualities of the powder. Examples of typical binders are lactose, starch and various sugars. "Lubricants" as used herein have several functions including preventing the adhesion of the tablets to the compression equipment and improving the flow of the granulation prior to compression or encapsulation. Lubricants are in most cases hydrophobic materials. Excessive use of lubricants can result in a formulation with reduced disintegration and/or delayed dissolution of the drug substance. "Glidants" as used herein are substances which improve the flow characteristics of the granulation material. Examples of glidants include talc and colloidal silicon dioxide. "Disintegrants" as used herein are substances or a mixture of substances added to a formulation to facilitate the breakup or disintegration of the solid dosage form after administration. Materials that serve as disintegrants include starches, clays, celluloses, algins, gums and cross-linked polymers. A group of disintegrants referred to as "super-disintegrants" generally are used at a low level in the solid dosage form, typically 1% to 10% by weight relative to the total weight of the dosage unit. Croscarmelose, crospovidone and sodium starch glycolate represent examples of a cross-linked cellulose, a cross-linked polymer and a cross-linked starch, respectively. Sodium starch glycolate swells seven- to twelve-fold in less than 30 seconds effectively disintegrating the granulations that contain it.

The disintegrant preferably used in the present invention is selected from the group comprising modified starches, croscarmallose sodium, carboxymethylcellulose calcium and crospovidone. A more preferred disintegrant in the present invention is a modified starch such as sodium starch glycolate.

Preferred carriers include capsules or compressed tablets which contain the solid pharmaceutical dosage forms described herein. Preferred capsule or compressed tablet forms generally comprise a therapeutically effective amount of Efavirenz and one or more disintegrants in an amount greater than about 10% by weight relative to the total weight of the contents of the capsule or the total weight of the tablet.

Preferred capsule formulations may contain Efavirenz present in an amount from about 5 to about 1000 mg per capsule. Preferred compressed tablet formulations contain Efavirenz in an amount from about 5 mg to about 800 mg per tablet. More preferred formulations contain about 50 to about 200 mg per capsule or compressed tablet. Preferably, the capsule or compressed tablet pharmaceutical dosage form comprises a therapeutically effective amount of Form 1, 2, 3, or 4 Efavirenz; a surfactant; a disintegrant; a binder; a lubricant; and optionally additional pharmaceutically acceptable excipients such as diluents, glidants and the like; wherein the disintegrant is selected from modified starches; croscarmallose sodium, carboxymethylcellulose calcium and crospovidone.

In general, liquid pharmaceutical compositions for oral administration have ranges of the HIV reverse transcriptase inhibitor agents which can vary from about 0.1 to about 15% by weight (wgt). More preferably, the drug substance component will range from about 1 to about 10% by weight in the composition.

For oral administration in liquid form, the crystalline Efavirenz can be combined with any oral, non-toxic pharmaceutically acceptable inert carrier such as ethanol, glycerol, water and the like. In a preferred liquid composition, the liquid vehicle consists of essentially polyol esters of medium chain fatty acids. This term polyol esters of medium chain fatty acids is intended to include esters and mixed esters of glycerol, propylene glycol or other open chain polyols such as polyethylene glycol, reacted with medium chain fatty acids, wherein said acid has a chain length between 6 and 12 carbon atoms. Particularly preferred for compositions are triglycerides or diglycerides of the $C_8$–$C_{10}$ fatty acids commercially available from the fractionation of coconut oil. Commercially available products of this description are sold under the trade names "Miglyol" and "Captex 300" which are described as having a typical composition of about 68% $C_8$ fatty acid (caprylic) triglyceride and about 28% $C_{10}$ fatty acid (capric) triglyceride with minor levels of $C_6$ and $C_{14}$ fatty acid triglycerides.

The medium chain fatty acid ester component, when present serves as the solvent vehicle for the active agent in formulating the compositions of the invention and is present in the composition in the range from about 50% to about 99%, by weight, but more preferably from 70% to 99% by weight.

Preferably, the liquid composition containing polyol esters will contain a sweetening agent which is useful in reducing the oily taste of the medium chain fatty acid ester and thus contributes in a significant way in making the compositions more palatable.

The sweetening agent can be selected from a sugar such as sucrose, mannitol, sorbitol, xylitol, lactose, etc. or a sugar substitute such as cyclamate, saccaharin, aspartame, etc. If sugar substitutes are selected as the sweetening agent the amount employed in the compositions of the invention will be substantially less than if sugars are employed. Taking this into account, the sweetening agent can be used in the composition in the range of from 0.1 to 50% by weight and more preferably in the range of 0.5 to 30% by weight.

The more preferred sweetening agents are the sugars and particularly sucrose. The particle size of the powdered sucrose used has been found to have a significant influence in the physical appearance of the finished composition and its ultimate acceptance for taste. The preferred particle size of the sucrose component when used is in the range of from 200 to less than 325 mesh US Standard Screen.

In another preferable liquid pharmaceutical composition, Efavirenz is combined with a liquid vehicle which is a vegetable oil selected from the class consisting of olive oil, peanut oil, soybean oil, corn oil, safflower oil, sunflower oil, canola oil, or walnut oil. These vegetable oils are commercially available from a number of sources well recognized by those skilled in the art.

The vegetable oil component serves as the solvent vehicle for the active agent in formulating the compositions of the invention and is present in the composition in the range from 50 to 99%, by weight more preferably from 70% to 99% by weight.

Preferably, the pharmaceutical compositions containing vegetable oil will also contain a sweetening agent which is useful in reducing the oily taste of the vegetable oil and thus contributes in a significant way in making the compositions more palatable.

The liquid compositions may also contain other components routinely utilized in formulating pharmaceutical compositions. One example of such components is lecithin. Its use in compositions of the invention as an emulsifying agent in the range of from 0.05 to 1% by weight, more preferably from 0.1 to 0.5% by weight may possibly serve to improve absorption of the active drug agent. Other examples of components that may be used are antimicrobial preservatives, such as benzoic acid or parabens; suspending agents, such as colloidal silicon dioxide; antioxidants; topical oral anesthetics; flavoring agents; and colorants.

The selection of such optional components and their level of use in the compositions of the invention is within the level of skill in the art and will be even better appreciated from the working examples provided hereinafter.

Crystalline Efavirenz may also be coupled with soluble polymers as targetable drug carriers. Such polymers can include polyvinylpyrrolidine pyran copolymer, polyhydroxypropylmethacrylamide-phenol, polyhydroxyethyl-aspartamidephenol or polyethylene oxide-polylysine substituted with palmitolyl residues. Furthermore, the crystalline Efavirenz may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

Gelatin capsules of crystalline Efavirenz contain Efavirenz and the liquid or solid compositions described herein. Gelatin capsules may also contain powdered carriers such as lactose, starch, cellulose derivatives, magnesium stearate, stearic acid and the like. Similar diluents can be used to make compressed tablets. Both tablets and capsules can be manufactured as sustained release products to provide for continuous release of medication over a period of hours. Tablets can be sugar coated or film coated to mask any unpleasant taste and to protect the tablet from the atmosphere or enteric coated for selective disintegration in the gastrointestinal track.

In general, water, a suitable oil, saline, aqueous dextrose (glucose), and related sugar solutions and glycols, such as propylene glycol or polyethylene glycols are suitable carriers for parenteral solutions. Solutions for parenteral solutions are prepared by dissolving the crystalline Efavirenz in the carrier and, if necessary, adding buffering substances. Anti-oxidizing agents such as sodium bisulfite, sodium sulfite, or ascorbic acid either alone or combined, are suitable stabilizing agents. Citric acid and its salts and sodium EDTA may also be employed. Parenteral solutions may also contain preservatives, such as benzalkonium chloride, methyl- or propyl-paraben and chlorobutanol.

Suitable pharmaceutical carriers are described in Remington's Pharmaceutical Sciences, Mack Publishing Co., a standard reference text in this field. Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

Nasal Spray

An aqueous solution is prepared such that each 1 milliliter contains 10 milligrams of active ingredient, 1.8 milligrams methylparaben, 0.2 milligram propylparaben and 10 milligrams methylcellulose. The solution is dispensed into 1 milliliter vials.

Lung Inhaler

A homogeneous mixture of the active ingredient in polysorbate 80 is prepared such that the final concentration of the active ingredient will be 10 milligrams per container and the final concentration of polysorbate 80 in the container will be 1% by weight. The mixture is dispensed into each can, the valves are crimped onto the can and the required amount of dichlorotetrafluoroethane is added under pressure.

Combination of components (a) and (b)

The Form 1, Form 2, Form 3, Form 4, Form 5 therapeutic agent component (a) of this invention can independently be in any dosage form, such as those described above, and can also be administered in various combinations, as described above. In the following description component (b) is to be understood to represent one or more agents as described previously. Thus, if components (a) and (b) are to be treated the same or independently, each agent of component (b) may also be treated the same or independently.

Components (a) and (b) of the present invention may be formulated together, in a single dosage unit (that is, combined together in one capsule, tablet, powder, or liquid, etc.) as a combination product. When component (a) and (b) are not formulated together in a single dosage unit, the component (a) may be administered at the same time as component (b) or in any order; for example component (a) of this invention may be administered first, followed by administration of component (b), or they may be administered in the reverse order. If component (b) contains more that one agent, e.g., one RT inhibitor and one protease inhibitor, these agents may be administered together or in any order. When not administered at the same time, preferably the administration of component (a) and (b) occurs less than about one hour apart. Preferably, the route of administration of component (a) and (b) is oral. The terms oral agent, oral inhibitor, oral compound, or the like, as used herein, denote compounds which may be orally administered. Although it is preferable that component (a) and component (b) both be administered by the same route (that is, for example, both orally) or dosage form, if desired, they may each be administered by different routes (that is, for example, one component of the combination product may be administered orally, and another component may be administered intravenously) or dosage forms.

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of components (a) and (b) of the present invention will be readily ascertainable by a medical practitioner skilled in the art, based upon the present disclosure. By way of general guidance, typically a daily dosage may be about 100 milligrams to about 1.5 grams of each component. If component (b) represents more than one compound, then typically a daily dosage may be about 100 milligrams to about 1.5 grams of each agent of component (b). By way of general guidance, when the compounds of component (a) and component (b) are administered in combination, the dosage amount of each component may be reduced by about 70–80% relative to the usual dosage of the component when it is administered alone as a single agent for the treatment of HIV infection, in view of the synergistic effect of the combination.

The combination products of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients.

Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose or other appropriate materials as known in the art, in order to further separate the active components. The polymer coating serves to form an additional barrier to interaction with the other component. In each formulation wherein contact is prevented between components (a) and (b) via a coating or some other material, contact may also be prevented between the individual agents of component (b).

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer.

Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Pharmaceutical kits useful for the treatment of HIV infection, which comprise a therapeutically effective amount of a pharmaceutical composition comprising a compound of component (a) and one or more compounds of component (b), in one or more sterile containers, are also within the ambit of the present invention. Sterilization of the container may be carried out using conventional sterilization methodology well known to those skilled in the art. Component (a) and component (b) may be in the same sterile container or in separate sterile containers. The sterile containers of materials may comprise separate containers, or one or more multi-part containers, as desired. Component (a) and component (b), may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

Obviously, numerous modifications and variations of the present invention are possible in light of the above teachings. It is therefore to be understood that within the scope of the appended claims, the invention may be practiced otherwise than as specifically described herein.

Analytical Methods x-Ray Powder Diffraction x-Ray powder diffraction data of Efavirenz were obtained with a Philips Model 3720 automated powder diffractometer. Samples were run in a batch mode with a Model PW 1775 multi-position sample changer. The diffractometer was equipped with a variable slit (θ-compensating slit), a scintillation counter and a graphite monochromator. The radiation was CuKα (40 kV, 30 mA). Data were collected at room temperature from 2 to 60 degrees 2θ; the step size was 0.02 degrees; the count time was 0.5 sec. per step. Samples were prepared on glass specimen holders as a thin layer of powdered material without solvent.

Differential Scanning Calorimetry

The thermal properties of Efavirenz were characterized with differential scanning calorimetry using a TA Instruments DSC 910, with data analysis via a TA Instruments Thermal Analyzer 2100. Samples were placed in sealed aluminum pans for analysis with an empty aluminum pan serving as the reference. Heating rates of 5° C. per minute or 10° C. per minute were employed over a temperature range of 25° C. to 200° C. The instrument was calibrated with a indium standard.

EXAMPLES

The following examples teach the preparation of (S)-6-chloro-4-cyclopropylethynyl-4-trifluoromethyl-1,4-dihydro-2H-3,1-benzoxazin-2-one.

Example 1

Preparation of N-(4-chlorophenyl)-2,2-dimethyl propanamide

4-Chloroaniline (52.7 kg, 413 mol) was dissolved in a mixture of t-butyl methyl ether (180 kg), 30% aqueous sodium hydroxide (61.6 kg, 463 mol) and water (24.2 kg), then cooled to 15° C. To the resulting slurry was charged trimethylacetyl chloride (52.2 kg, 448 mol) over 1 h, keeping the temperature below 40° C. After stirring 30 min at 30° C. the slurry was cooled to −10° C. and held for 2 hours. The product was collected by filtration, washed with a solution of 90/10 water/methanol (175 kg), then dried in vacuo to give 85 kg (97% yield) of the title compound as a crystalline solid: mp 152–153° C.; $^1$H NMR (300 MHz, CDCl$_3$) δ 7.48 (d, J=9 Hz, 2H) 7.28 (d, J=9 Hz, 2H); $^{13}$C NMR (75 MHz, CDCl$_3$) d 176.7, 136.6, 129.1, 128.9, 121.4, 39.6, 27.6.

Example 2

Preparation of 4-Chloro-2-trifluoroacetyl-aniline, Hydrochloride Hydrate

N-(4-Chlorophenyl)-2,2-dimethyl propanamide (36.7 kg, 173 mol) was charged to a solution of TMEDA (20.2 kg, 174 mol) in anhydrous t-butyl methyl ether (271.5 kg) and cooled to −20° C. To the cold slurry was added 2.7 N n-butyllithium in hexane (101.9 kg, 393 mol) while keeping the temperature below 5° C. After aging 2 hr at 0 to 5° C., the solution was cooled below −15° C. then rapidly reacted with ethyl trifluoroacetate (34.5 kg, 243 mol). After 30 min, the resulting solution was quenched into 3N HCl (196 L, 589 mol) keeping the temperature below 25° C. After removal of the aqueous phase, the organic solution was concentrated by distilling approximately 200 L of solvent. Acetic acid (352 kg) was added while distilling 325 kg solvent under 100 mm vacuum. After cooling the solution to 30° C., 12 N HCl (43.4 kg, 434 mol) was added and the mixture heated to 65 to 70° C. and held 4 hours. The resulting slurry was cooled to 5° C. and the product was collected by filtration, washed with ethyl acetate (50.5 kg) and dried in vacuo to give 42.1 kg (87%) of the title compound as a white crystalline solid: mp 159–162 dec; $^1$H NMR (300 MHz, DMSO-d$_6$) d 7.65–7.5 (complex, 2H), 7.1 (d, J=8 Hz, 1H), 7.0 (brs, 3H); $^{19}$F NMR (282 MHz, DMSO-d$_6$) δ −69.5.

Example 3

Preparation of N-((4'-Methoxy)benzyl)-4-chloro-2-trifluoroacetylaniline

To a slurry of 4-Chloro-2-trifluoroacetylaniline, hydrochloride hydrate (40.0 kg, 144 mol) in toluene (140 kg) and water (50 L) was added 30% NaOH (18 kg) to pH 7.0. After removing the aqueous phase, 4-methoxybenzyl alcohol (20 kg, 144 mol) and TsOH (1.0 kg, 5.3 mol) were added. The solution was heated to reflux and the water/toluene azeotrope (30 L) distilled. The solution was cooled to room temperature and washed with saturated brine (80 kg). The organic solution was concentrated in vacuo to a volume of 35–40 L, then diluted with THF (52 kg). The weight percent of the title compound in toluene/THF was calculated by HPLC to be 43%. The yield based on HPLC weight % analysis was 47.7 kg (96%). An analytical sample was obtained by removing the solvent in vacuo and recrystallizing from heptane: mp 82–84° C.; $^1$H NMR (300 MHz, CDCl$_3$) δ 9.04 (s,1H), 7.74 (d, J=2 Hz, 1H), 7.35 (dd, J=2, 9 Hz), 7.24 (d, J=8 Hz, 2H), 6.91 (d, J=8 Hz, 2H), 6.75 (d, J=9 Hz, 1H), 4.43 (d, J=6 Hz, 2H), 3.79 (s, 3H); $^{13}$C NMR (75 MHz, CDCl$_3$) δ 180.5, 159.2, 151.9, 137.4, 130.8, 128.9, 128.4, 119.9, 117.0, 114.5, 114.4, 111.3, 55.3, 46.6.

Example 3a

Synthesis of (1R,2S)-Pyrrolidinyl norephedrine

To a mixture of n-butanol (227 kg), water (144 kg) and potassium carbonate (144 kg, 1043 mol), was added (1R, 2S)-norephedrine (68.6 kg, 454 mol). The mixture was heated to 90° C. and 1,4-dibromobutane (113.4 kg, 525 mol) was added over 2 hours. The reaction was refluxed 5 h then cooled to 40° C. Water (181 kg) was added and the phases separated at 30° C. To the organic phase was added 12 N HCl (54.3 kg, 543 mol). The solution was heated to reflux and 150 L of distillate removed at 200 to 300 mm. Toluene (39.5 kg) was added at 70° C. and the resulting slurry cooled to 0–5° C. for crystallization. The product was collected, washed twice with toluene (39 kg each) and dried under a nitrogen purge to give 83.6 kg of the title compound as its hydrochloride salt. The hydrochloride salt was charged to toluene (392 kg) and water (42 kg) and treated with 30% NaOH (approximately 55 kg, 414 mol) to a pH greater than 12. After removal of the lower aqueous phase, the organic solution was partially concentrated by distilling 140 L of solvent to give a 20 wt % solution of the title compound in toluene. The calculated yield was 50 kg (75%). An analytical sample was obtained by concentrating the toluene solution of the title compound in vacuo then recrystallizing from heptane: mp 46–48° C.

Example 3b

Preparation of cyclopropylacetylene

A mixture of 5-chloro-1-pentyne (23.0 kg, 224 mol) and anhydrous THF (150 kg) is cooled to −20° C. n-Hexyllithium (2.3 eq.; 158 kg of 30 wt. %) in hexane is added into the mixture at such a rate as to not allow the temperature to go over 50° C. (approximately 2 hours). During the second half of the n-hexyllithium addition the temperature must remain above −5° C. to prevent an accumulation of the organolithium and a dangerously exothermic induction reaction. The reaction is aged at −5 to 0° C. for 2 hours, until GC analysis indicates at least 99% conversion. Toluene (35 to 40 kg) is then added and the reaction is concentrated under vacuum until the volume is reduced to ~⅓ of original volume. The mixture is heated (to ~40° C.) over the course of the concentration to maintain a good rate of distillation. The mixture is then cooled to 15 to −20° C. and a solution of ammonium chloride (11 to 12 kg) in 50 to 60 L water is added at such a rate as to not allow the temperature to go above 10° C. After separation of the aqueous layer (approximately 70 kg), the reaction mixture is circulated through a tower containing 15 kg of 3Å molecular sieves until the water content is ~300 ppm or lower as determined by Karl Fisher analysis. The dried organic solution is then distilled through a column packed with steel wool at atmospheric pressure, collecting cyclopropylacetylene as a solution in THF/toluene/hexane. The calculated yield is 14.0 kg.

Example 4

Preparation of (S)-5-Chloro-α-(cyclopropylethynyl)-2-[(4-methoxyphenyl)methyl]-amino]α-(trifluoromethyl)benzenemethanol To a toluene solution of (1R,2S)-pyrrolidinyl norephedrine (80 kg, containing 60.7 mol (1R,2S)-pyrrolidinyl norephedrine) was charged triphenylmethane (100 g). The solution was concentrated in vacuo to about half the original volume. Anhydrous THF (35 kg) was added and the solution chilled with the cooling jacket set at −50° C. When the temperature reached −20° C., n-hexyllithium (33 wt % in hexanes, 33.4 kg, 119.5 mol) was charged while maintaining the temperature below 0° C. To the resulting red solution was charged a solution of cyclopropylacetylene (30 wt % in THF/hexanes/toluene; containing about 4 kg, 65 mol of cyclopropylacetylene) while maintaining an internal temperature below −20° C. The resultant solution was aged at −45 to −50° C. for 1 hour. To the cold solution was charged a solution of N-((4'-Methoxy)benzyl)-4-chloro-2-trifluoroacetylaniline(43 wt % in THF/toluene; containing about 10 kg, 28.8 mol of N-((4'-Methoxy)benzyl)-4-chloro-2-trifluoroacetylaniline) while maintaining a reaction temperature below −40° C. After aging the mixture at −43+/−3° C. for 1 h, the reaction was quenched into 140 kg 1N HCl, pre-chilled to 0° C. The organic layer was separated and extracted twice with 25 kg portions of 1N HCl, twice with 40 kg water, then concentrated in vacuo to a volume of about 29 L. Toluene (47 kg) was added and the solution concentrated to a volume of 28 to 30 L. Heptane (23 kg) was charged and the mixture cooled and held at −5° C. for 4 hours. The product was filtered, washed twice with 10 kg portions of heptane and dried in vacuo to give 10 kg (85%) of the title compound as an off-white solid: mp 163–165° C.; $[\alpha]^{25}D$ +8.15° (c 1.006, MeOH); $^1$H NMR (300 MHz, CDCl$_3$) δ 7.55 (brs, 1H), 7.23 (d, J=8 Hz, 2H), 7.13 (dd, J=3, 9 Hz, 1H), 6.86 (d, J=8 Hz, 2H), 6.59 (d, J=8 Hz, 1H), 4.95 (bs, 1H), 4.23 (s, 2H), 3.79 (s,3H), 2.39 (m, 1H), 1.34 (m, 1H), 0.84 (m, 2H), 0.76 (m,2H); $^{13}$C NMR (75 MHz, CDCl$_3$) δ 158.9, 145.5, 130.6, 130.3, 130.2, 128.6, 125.9, 122.0, 121.6, 119.5, 114.8, 114.1, 94.0, 75.2, 74.7, 70.6, 55.3, 48.0, 8.6, 8.5, −0.6; $^{19}$F NMR (282 MHz, CDCl$_3$) δ 80.19.

Example 5

Preparation of (S)-6-Chloro-4-(cyclopropylethynyl)-1,4-dihydro-4-(trifluoromethyl)-2-(4'-methoxyphenyl)-3,1-benzoxazine To a solution of heptane (295.5 kg) and ethyl acetate (32.5 kg) was added p-chloranil (57 kg, 232 mol) and (S)-5-Chloro-α-(cyclopropylethynyl)-2-[(4-methoxyphenyl)methyl]-amino]-α-(trifluoromethyl)benzenemethanol (89 kg, 217 mol). The mixture was refluxed with good agitation for 5.5 h then diluted with ethyl acetate (64.1 kg) and cooled to 30° C. Tetracholorophydroquinone was removed by filtration and washed with a mixture of heptane (104.7 kg) and ethyl acetate (31 kg). The filtrate was partially concentrated by distillation of 260 L solvent, then diluted with heptane (177 kg) and cooled to −10 to −15° C. The resulting slurry was filtered and the product washed with heptane (41 kg) and dried on the filter to less than 20 wt % heptane (by loss on drying). The yield calculated by HPLC, was 71 kg (80%). An analytical sample was obtained by trituration of the sample with IN NaOH, followed by recrystallization from hexane/ethyl acetate: mp 130–131.7° C.; 1H NMR (300 MHz, DMSO-d$_6$) δ 7.46 (d, J=9 Hz, 2H), 7.28–7.21 (m, 3H), 7.0 (d, J=9 Hz, 2H), 6.85 (d, J=9 Hz, 1H), 5.52 (s, 1H), 3.78 (s, 3H), 1.52–1.47 (m, 1H), 0.90–0.84 (m, 2H), 0.72–0.68 (m, 1H); $^{13}$C NMR (75 MHz, DMSO-d$_6$) δ 160.3, 143.8, 129.6, 129.3, 128.9, 125.8, 123.1, 121.7, 118.1, 117.8, 113.8, 93.6, 80.9, 74.1, 70.3, 55.2, 8.5, 8.4, −1.07; $^{19}$F NMR (282 MHz, CDCl$_3$) δ 157.5.

Example 6

(S)-5-Chloro-α-(cyclopropylethynyl)-2-amino-α(trifluoromethyl)benzenemethanol

Crude (S)-5-Chloro-4-(cyclopropylethynyl)-1,4-dihydro-4-(trifluoromethyl)-2-(4'methoxyphenyl)-3,1-benzoxazine (71 kg calculated dry weight) was charged to a mixture of methanol (301 kg), 30% NaOH (121 kg) and water (61 L).

The mixture was heated to 60° C. to give a clear solution then cooled to 30° C. A solution of sodium borohydride (3.2 kg, 84.2 mol) in 0.2 N NaOH (29 L) was added to the methanolic solution over 20 min, keeping the temperature below 35° C. After 30 min, excess borohydride was quenched with acetone (5.8 kg) and the solution diluted with water (175 L) then neutralized to pH 8 to 9 with acetic acid. The resulting slurry was cooled to about 0° C., filtered and the product washed with water then dried in vacuo at 40° C. The crude product was reslurried with a mixture of toluene (133 kg) and heptanes (106 kg) initially at 25° C., then with cooling below −10° C. The product was filtered, washed with heptanes (41 kg) and dried in vacuo at 40° C. to give 44.5 kg (88%) as an off-white/pale yellow crystalline solid. An analytical sample was recrystallized from t-butyl methyl ether/heptane: mp 141–143° C.; $[\alpha]^{25}D$ −28.3° (c0.106, MeOH); 1H NMR (300 MHz, CDCl$_3$) δ 7.54 (d, J=2 Hz, 1H), 7.13 (dd, i=9, 2 Hz, 1H), 6.61 (d, J=9 Hz, 1H), 4.61 (brs, 1H), 4.40 (brs, 1H), 1.44–135 (m, 1H), 0.94–0.78 (m, 2H): $^{13}$C NMR (75 MHz, DMSO-d$_6$) δ 146.7, 129.4, 129.0, 124.3, 118.4, 118.07, 118.05, 92.3, 72.6, 71.0, 8.2, 8.1, −1.1; $^{19}$F NMR (282 MHz CDCl$_3$) δ −80.5.

Example 7

Preparation of (S)-6-Chloro-4-(cyclopropylethynyl)-1,4-dihydro-4-(trifluoromethyl)-2H-3,1-benzoxazine-2-one (S)-5-Chloro-α-(cyclopropylethynyl)-2-amino-(trifluoromethyl)benzenemethanol (15.7 kg, 54.3 mol) was dissolved in a mixture of heptanes (32 kg) and THF (52 kg) below −10° C. Phosgene (~8.0 kg, 80 mol) was directly fed below the surface over about 1 h, keeping the temperature below 0° C. The resulting slurry was warmed to 20–25° C. and held 1 hour. Methanol (6.5 kg, 203 mol) was added and the solution stirred about 30 min. Heptanes (97 kg) was added and ~140 L of solvent was distilled under reduced pressure. Heptanes (97 kg) and THF (22 kg) were added and the solution washed with 5% aqueous sodium bicarbonate (15 L), followed by water (15 L). The solution was warmed to 50° C. and filtered into a clean reactor, followed by a 40 kg heptanes rinse. The solution was concentrated under reduced pressure, diluted with heptanes (22 kg) and cooled below −10° C. The product was filtered, washed with heptanes (37 kg) and dried in vacuo at 90–100° C. to give 16.0 kg (95%) as an off-white to slightly pinkish solid. HPLC: 99.8 area %: mp 139–141° C.; $[\alpha]^{25}D$ −94.10 (c 0.300, MeOH); 1H NMR (400 MHz, DMSO-d$_6$) δ 11.05 (s, 1H), 7.54 (dd, J=2.5, 7 Hz, 1H), 7.43 (d, J=2.5 Hz, 1H), 6.99 (d, J=7 Hz, 1H), 51.58 (m, 1H), 0.92 (m, 2H), 0.77 (m, 2H); $^{13}$C NMR (100 MHz, DMSO-d$_6$) δ 146.23, 134.71, 132.04, 126.93, 126.57, 122.24, 116.83, 114.08, 95.63, 77.62, 65.85, 8.48, 8.44, −1.32; $^{19}$F NMR (282 MHz, DMSO-d$_6$) δ −81.1.

Examples 8–16 specifically teach the preparation of each of the forms of Efavirenz of the present invention, as well as methods to effectuate the interconversions of these forms (Scheme 5). The following examples are meant to be illustrative of the present invention, and not should not be taken as limiting the inventors scope.

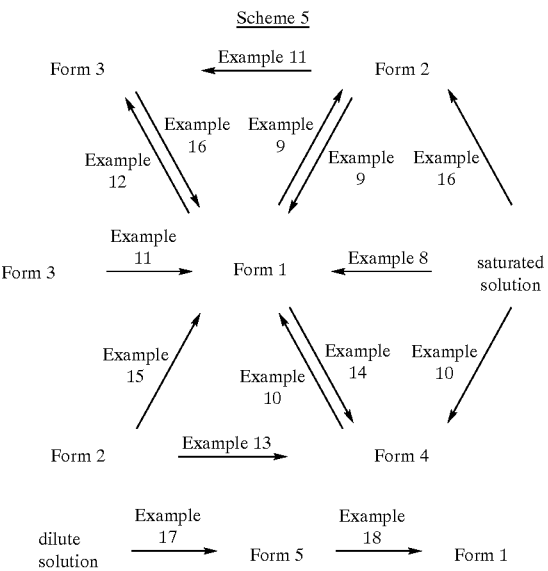

Scheme 5

Example 8

Direct Crystallization of Form I

Efavirenz (800 g, 2.5 mol) was dissolved in THF (1.2 L) and heptane (6.8 L). The solution was clarified by filtration through a #1 Whatman paper. The THF was then removed by distillation at atmospheric pressure, as the volume was maintained constant by replacing with fresh heptane. When the level of the THF was <1%, the solution was cooled to 70° C. and seeded. The solution was further cooled and the crystallization started at 64° C. A sample indicated form I by XRD. The slurry was further cooled to 30° C. and filtered. The wet cake was dried at 65° C. in a vacuum oven with nitrogen purge until a loss on drying of 0.36% to yield 640 g of product (80%yield).

Example 9

Crystallization of Form 2, Conversion to Form 1

Efavirenz (450 g, 1.4 mol) was slurried in heptane (3.5 L) and heated to reflux until complete dissolution. The solution was allowed to cool to 73° C., at which point it was filtered through #1 Whatman paper and cooled to 6° C. The thin slurry was filtered and the wet cake was washed with 300 mL of heptane. The wet cake (389 g) was dried in a vacuum tray oven at 100° C. for 15 hours to yield 388 g (86% yield) of Form 1.

Example 10

Crystallization of Form 4, Conversion to Form 1

Efavirenz (32 g, 0.1 mol) was dissolved in 390 mL heptane and 20 mL of THF at 60° C. The solution was allowed to cool down and at 45° C. it was seeded with 50mg of DMP 266. After crystallization occurred, solvent was removed in vacuo and it was replaced with fresh heptane. The slurry was cooled to 0° C. and filtered. XRD indicated form IV. It was dried in a vacuum oven at 80° C. for 16 hours to yield 26 g of Form 1 (82% yield).

Example 11

Crystallization of Form 2, Conversion to Form 3, Conversion to Form 1

Efavirenz (105 g, 0.33 mol) was slurried in 1.2 L of heptane and heated to reflux until dissolution. The solution was allowed to cool to 75° C. and it was filtered through #1 Whatman paper and cooled. A thin slurry crystallized, and a sample was filtered. x-Ray powder diffraction indicated Form 2. The slurry was stirred at room temperature for 24 hours and the resulting thick slurry was diluted with 200 mL of heptane, filtered and dried under vacuum at room temperature to yield 82.5 g (79%). The solid was identified as Form 3 by X-ray powder diffraction. A 5 g sample was dried at 90° C. for 24 hours and the resulting solid was identified as form I by X-ray powder diffraction.

Example 12

Conversion of Form 1 to Form 3

Efavirenz Form 1 (105 g, 0.33 mol) was slurried in 1.0 L of heptane at room temperature for seven days. A sample indicated no Form 1 present by XRD. The peaks obtained were the same as the one obtained starting from Form 2, although relative intensities were slightly different.

Example 13

Conversion of Form 2 to Form 4

Efavirenz Form 2 (50 g, 0.16 mol) was slurried in 580 mL of heptanes. THF (7 mL, resulting in 1% THF in heptane) was added, heated to 40° C. and after 50 minutes a sample of the slurry was filtered and XRD (X-ray powder diffraction) still indicated Form 2. THF (28 mL, total 32 mL, resulting in 5% THF in heptane) was added in four portions. After the addition of the last portion, the mixture was cooled to 28° C., at which point a very thick slurry formed, confirmed to be Form 4 by XRD.

Example 14

Conversion of Form 1 to Form 4

Efavirenz Form 1 (10 g, 0.03 mol) was slurried in 90 mL of heptane. The slurry was heated to 35° C. THF was added in 2 mL portions. After the addition of a total of 6 mL (resulting solution 6% THF), the slurry became very thick. XRD indicated Form 4.

Example 15

Conversion of Form 2 to Form 1 by Heating a Slurry to 70° C.

Efavirenz Form 2 (3 g, 0.01 mol) was slurried in heptane (42 mL), heated to 70° C. and held for 2 hours. The slurry was cooled down to room temperature and a sample was filtered for XRD, indicating Form 1 only.

Example 16

Conversion of Form 3 to Form 1 by Heating a Slurry to 70° C.

Efavirenz Form 1 (3 g, 0.01 mol) was slurried in heptane (42 mL) for 48 hours. XRD indicated Form 3. The slurry was then heated to 70° C., held for 2 hours, cooled to room temperature and a sample filtered for XRD, which indicated Form 1.

Example 17

Direct Crystallization of Form 5

Efavirenz Form 1 (approximately 70 g) was slurried in 1 L of 1% v/v THF/heptane at room temperature. Undissolved solids were removed by filtration and the mother liquor was seeded at room temperature with Form 5. Crystals formed slowly and were isolated by filtration, yielding 0.92 g of Form 5. The solid was identified as Form 5 by X-ray powder diffraction.

Alternatively, Efavirenz Form 1 (approximately 70 g) was slurried in 1.5 L of 1% v/v THF/heptane and warmed to 40° C. The solution was filtered warm (40° C.) to remove any undissolved solids and the mother liquor was seeded with Form 5 at 40° C. As the solution cooled to room temperature, Form 5 crystallized. The solid was isolated by filtration at room temperature (9.43 g).

Alternatively, Efavirenz Form 1 (approximately 70g) was slurried in 1 L of warm heptane and 10 mL of THF was added to adjust the solvent ratio to 1% v/v THF/heptane. The slurry was then heated to total dissolution at 85° C. As the solution cooled, it was seeded periodically with Form 5 until the seeds no longer dissolved (63° C.), then allowed to cool to 45° C. and filtered. The solid isolated was Form 1. The solution was then allowed to cool to room temperature overnight and Form 5 crystals were then collected by filtration (15.41g).

Example 18

Conversion of Form 5 to Form 1

Form 5 was dried at 95° C. for 3 days in a vacuum oven with a nitrogen purge to give Form 1 which was identified by X-ray powder diffraction.

What is claimed is:

1. Form 2 of crystalline Efavirenz which is characterized by an x-ray powder diffraction pattern substantially in accordance with that shown in FIG. 2.

2. The compound of claim 1, in substantially pure form.

3. The compound of claim 2, wherein substantially pure is greater than 90 percent pure.

4. The compound of claim 1, which is characterized by an x-ray powder diffraction pattern comprising four or more 2θ values selected from the group consisting of: 6.8±0.2, 9.2±0.2, 12.3±0.2, 16.2±0.2, 21.4±0.2, 22.7±0.2, 24.1±0.2, and 28.0±0.2.

5. The compound of claim 1 which is characterized by a differential scanning calorimetry thermogram having a peak at about 116° C. to about 119° C.

6. The compound of claim 1, which is characterized by a differential scanning calorimetry thermogram substantially in accordance with that shown in FIG. 6.

7. The compound of claim 4, which is further characterized by a differential scanning calorimetry thermogram having a peak at about 116° C. to about 119° C.

8. A method for inhibiting viral replication by a virally encoded reverse transcriptase which comprises providing the compound of claim 1, in an amount sufficient to result in the HIV reverse transcriptase being contacted with an effective inhibitory amount of the active drug substance.

9. A method for the treatment of human immunodeficiency virus infection which comprises administering to a host in need of such treatment a therapeutically effective amount of a compound of claim 1.

10. The method of claim 9, wherein the compound is administered at a dose of about 1 mg to about 1000 mg.

11. The compound of claim 1 prepared by the process of rapid crystallization from a saturated alkane solution of Efavirenz.

12. The process of claim 11, wherein rapid crystallization comprises:

1) dissolving Efavirenz in a suitable solvent at a suitable temperature to give a saturated solution;

2) filtering the saturated solution; and
3) cooling the saturated solution rapidly to produce Form 2 crystalline Efavirenz.

13. The process of claim 12, wherein the suitable solvent for rapid crystallization is heptane, the suitable temperature is about 70° C. to about 80° C., and cooling the saturated solution rapidly comprises contacting the saturated solution with a cold surface.

14. A process for preparing Form 4 of crystalline Efavirenz which is characterized by a differential scanning calorimetry thermogram substantially in accordance with that shown in FIG. 8, the process comprising:
1) adding a suitable second solvent to a solution of Efavirenz in a first solvent to produce a final solution;
2) distilling the final solution to a solvent composition from which Efavirenz crystallizes as Form 4 crystals; and
3) isolating the crystals.

15. The process of claim 14, wherein the suitable second solvent is heptane, the first solvent is tetrahydrofuran, the solvent composition is about 1 to about 10 percent tetrahydrofuran in heptane, and isolating comprises filtering.

16. Form 5 of crystalline Efavirenz which is characterized by an x-ray powder diffraction pattern comprising four or more 2θ values selected from the group consisting of: 10.2±0.2, 11.4±0.2, 11.6±0.2, 12.6±0.2, 19.1±0.2, 20.6±0.2, 21.3±0.2, 22.8±0.2, 24.8±0.2, 27.4±0.2, 28.2±0.2, and 31.6±0.2.

17. The compound of claim 16 in substantially pure form.

18. The compound of claim 16, which is characterized by a differential scanning calorimetry thermogram having a peak at about 108° C. to about 110° C.

19. A method for inhibiting viral replication by a virally encoded reverse transcriptase which comprises providing the compound of claim 16, in an amount sufficient to result in the HIV reverse transcriptase being contacted with an effective inhibitory amount of the active drug substance.

20. A method for the treatment of human immunodeficiency virus infection which comprises administering to a host in need of such treatment a therapeutically effective amount of the compound of claim 16.

21. The method of claim 20, wherein the compound is administered at a dosage from about 1 to about 1000 mg per dose.

22. The compound of claim 16 prepared by recrystallization from a mixed solvent system.

23. A method of treating HIV infection which comprises administering, in combination, to a host in need thereof a therapeutically effective amount of:
(a) a compound of claim 1 or 16; and
(b) at least one compound selected from the group consisting of HIV reverse transcriptase inhibitors and HIV protease inhibitors.

24. Form 2 of crystalline Efavirenz which is characterized by an differential scanning calorimetry thermogram substantially in accordance with that shown in FIG. 6.

25. The compound of claim 24 in substantially pure form.

26. The compound of claim 25, wherein substantially pure is greater than 90 percent pure.

27. The compound of claim 24, which is characterized by a differential scanning calorimetry thermogram having a peak at about 116° C. to about 119° C.

28. A method for inhibiting viral replication by a virally encoded reverse transcriptase which comprises providing the compound of claim 24, in an amount sufficient to result in the HIV reverse transcriptase being contacted with an effective inhibitory amount of the active drug substance.

29. A method for the treatment of human immunodeficiency virus infection which comprises administering to a host in need of such treatment a therapeutically effective amount of a compound of claim 24.

30. The method of claim 29, wherein the compound is administered at a dose of about 1 mg to about 1000 mg.

31. The compound of claim 24 prepared by the process of rapid crystallization from a saturated alkane solution of Efavirenz.

32. The process of claim 31, wherein rapid crystallization comprises:
1) dissolving Efavirenz in a suitable solvent at a suitable temperature to give a saturated solution;
2) filtering the saturated solution; and
3) cooling the saturated solution rapidly to produce Form 2 crystalline Efavirenz.

33. The process of claim 32, wherein the suitable solvent for rapid crystallization is heptane, the suitable temperature is about 70° C. to about 80° C., and cooling the saturated solution rapidly comprises contacting the saturated solution with a cold surface.

34. Form 5 of crystalline Efavirenz which is characterized by a differential scanning calorimetry thermogram having a peak at about 108° C. to about 110° C.

35. The compound of claim 34 substantially pure form.

36. A method for inhibiting viral replication by a virally encoded reverse transcriptase which comprises providing the compound of claim 34, in an amount sufficient to result in the HIV reverse transcriptase being contacted with an effective inhibitory amount of the active drug substance.

37. A method for the treatment of human immunodeficiency virus infection which comprises administering to a host in need of such treatment a therapeutically effective amount of the compound of claim 34.

38. The method of claim 37, wherein the compound is administered at a dosage from about 1 to about 1000 mg per dose.

39. The compound of claim 34 prepared by recrystallization from a mixed solvent system.

40. A method of treating HIV infection which comprises administering, in combination, to a host in need thereof a therapeutically effective amount
(a) a compound of claim 24 or 34; and
(b) at least one compound selected from the group consisting of HIV reverse transcriptase inhibitors and HIV protease inhibitors.

41. Form 2 of crystalline Efavirenz which is characterized by an x-ray powder diffraction pattern comprising four or more 2θ values selected from the group consisting of: 6.8±0.2, 9.2±0.2, 12.3±0.2, 16.2±0.2, 21.4±0.2, 22.7±0.2, 24.1±0.2, and 28.0±0.2.

42. A process for preparing Form 1 of crystalline Efavirenz, which is characterized by an x-ray powder diffraction pattern substantially in accordance with that shown in FIG. 1, the process comprising:
1) crystallizing Form 4 of crystalline Efavirenz from a solution of THF/heptane wherein the solution of THF/heptane is at about a 5% concentration of THF and is reduced to about a 1% concentration of THF; and
2) heating Form 4 of crystalline Efavirenz to a temperature of about 80° C. to about 100° C.

43. A process for preparing Form 1 of crystalline Efavirenz, which is characterized by an x-ray powder diffraction pattern comprising four or more 2θ values selected from the group consisting of: 6.0±0.2, 6.3±0.2, 10.3±0.2, 10.8±0.2, 14.1±0.2, 16.8±0.2, 20.0±0.2, 20.5±0.2, 21.1±0.2, and 24.8±0; the process comprising:

1) crystallizing Form 4 of crystalline Efavirenz from a solution of THF/heptane wherein the solution of THF/heptane is at about a 5% concentration of THF and is reduced to about a 1% concentration of THF; and 2) heating Form 4 of crystalline Efavirenz to a temperature of about 80° C. to about 100° C.

44. A process for preparing Form 1 of crystalline Efavirenz, which is characterized by a differential scanning calorimetry thermogram having a peak at about 138° C. to about 140° C., the process comprising:

1) crystallizing Form 4 of crystalline Efavirenz from a solution of THF/heptane wherein the solution of THF/heptane is at about a 5% concentration of THF and is reduced to about a 1% concentration of THF; and 2) heating Form 4 of crystalline Efavirenz to a temperature of about 80° C. to about 100° C.

45. A process for preparing Form 1 of crystalline Efavirenz, which is characterized by a differential scanning calorimetry thermogram substantially in accordance with that shown in FIG. 5, the process comprising:

1) crystallizing Form 4 of crystalline Efavirenz from a solution of THF/heptane wherein the solution of THF/heptane is at about a 5% concentration of THF and is reduced to about a 1% concentration of THF; and 2) heating Form 4 of crystalline Efavirenz to a temperature of about 80° C. to about 100° C.

* * * * *

UNITED STATES PATENT AND TRADEMARK OFFICE
CERTIFICATE OF CORRECTION

PATENT NO. : 6,673,372 B1
DATED : January 6, 2004
INVENTOR(S) : Lilian A. Radesca et al.

It is certified that error appears in the above-identified patent and that said Letters Patent is hereby corrected as shown below:

<u>Title page,</u>
Item [75], Inventors, should read as follows:
-- Lilian A. Radesca, Newark, DE;
  Michael B. Maurin, Wilmington, DE;
  Shelley R. Rabel, Landenberg, PA;
  James R. Moore, Newark, DE --

Signed and Sealed this

Thirteenth Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,673,372 B1  Page 1 of 1
APPLICATION NO. : 09/329421
DATED : January 6, 2004
INVENTOR(S) : Lilian A. Radesca et al.

It is certified that error appears in the above-identified patent and that said Letters Patent is hereby corrected as shown below:

Title page, column 2 Item [57] (Abstract), delete "are-designated" and insert -- are designated --, therefor.

At column 28, line 37, in Claim 4, delete "four" and insert -- five --, therefor.

At column 29, line 24, in Claim 16, delete "four" and insert -- six --, therefor.

At column 29, line 26, in Claim 16, after "11.6±0.2," delete "12.6±0.2,".

At column 30, line 42, in Claim 40, after "amount" insert -- of: --.

At column 30, line 48, in Claim 41, delete "four" and insert -- five --, therefor.

Signed and Sealed this
Seventeenth Day of April, 2012

David J. Kappos
*Director of the United States Patent and Trademark Office*